(12) United States Patent
Laflamme et al.

(10) Patent No.: US 10,371,685 B2
(45) Date of Patent: Aug. 6, 2019

(54) METHOD, DEVICE AND APPARATUS FOR MONITORING HALOGEN LEVELS IN A BODY OF WATER

(71) Applicant: GECKO ALLIANCE GROUP INC., Québec (CA)

(72) Inventors: Benoit Laflamme, Québec (CA); André Villemaire, Québec (CA); Jean-François Gravel, Québec (CA); Serge Caron, Québec (CA)

(73) Assignee: GECKO ALLIANCE GROUP INC., Québec (CA)

( * ) Notice: Subject to any disclaimer, the term of this patent is extended or adjusted under 35 U.S.C. 154(b) by 0 days.

(21) Appl. No.: 16/256,105

(22) Filed: Jan. 24, 2019

(65) Prior Publication Data
US 2019/0154649 A1    May 23, 2019

Related U.S. Application Data

(63) Continuation of application No. 15/460,394, filed on Mar. 16, 2017, now Pat. No. 10,228,359.

(51) Int. Cl.
*G01N 33/18* (2006.01)
*G01N 21/31* (2006.01)
(Continued)

(52) U.S. Cl.
CPC .............. *G01N 33/182* (2013.01); *E04H 4/00* (2013.01); *E04H 4/1281* (2013.01);
(Continued)

(58) Field of Classification Search
CPC ...... G01J 3/0205; G01J 3/0291; G01J 3/0297; G01J 3/42; G01J 2003/421;
(Continued)

(56) References Cited

U.S. PATENT DOCUMENTS 3,413,199 A    11/1968 Morrow et al.
3,966,413 A    6/1976 Marinenko
(Continued)

FOREIGN PATENT DOCUMENTS

CA    2430862    11/2007
CA    2324598    5/2008
(Continued)

OTHER PUBLICATIONS

Written Opinion of the International Searching Authority dated Jan. 13, 2011 in connection with International Patent Application PCT/CA2010/000775, 4 pages.
(Continued)

*Primary Examiner* — Michael C Bryant

(57) ABSTRACT

A method and an apparatus are presented for monitoring a concentration of a specific halogen in a body of water such as a spa or bathing unit for example. The apparatus comprises a housing in which is positioned an optical absorption analyzer for making first and second measurement of transmission of ultraviolet light from a light source emitting light at a specific wavelength. The second and first measurements are taken respectively before and after the ultraviolet light has travelled through a sample of water and are used to derive a concentration of the specific halogen. The derived concentration may then be communicated to a user using a display device and/or may be used to control operational components of a bathing unit for adjusting the concentration of halogen in the water. In some practical implementations, the apparatus may be embodied as a standalone device, which may be configured to float on the water of the bathing unit or, alternatively, may be configured for being installed in-line in a water circulation path of the bathing input by connecting the housing to circulation piping.

24 Claims, 15 Drawing Sheets

(51) Int. Cl.

| | | |
|---|---|---|
| *G01N 21/27* | (2006.01) | |
| *G01N 21/33* | (2006.01) | |
| *E04H 4/12* | (2006.01) | |
| *G01J 3/02* | (2006.01) | |
| *G01J 3/42* | (2006.01) | |
| *E04H 4/00* | (2006.01) | |
| *C02F 103/42* | (2006.01) | |
| *G01N 21/85* | (2006.01) | |
| *G01J 3/28* | (2006.01) | |

(52) U.S. Cl.
CPC ........... *G01J 3/0205* (2013.01); *G01J 3/0291* (2013.01); *G01J 3/0297* (2013.01); *G01J 3/42* (2013.01); *G01N 21/274* (2013.01); *G01N 21/3103* (2013.01); *G01N 21/3151* (2013.01); *G01N 21/33* (2013.01); *C02F 2103/42* (2013.01); *C02F 2209/11* (2013.01); *C02F 2209/29* (2013.01); *G01J 2003/2869* (2013.01); *G01J 2003/421* (2013.01); *G01N 21/85* (2013.01); *G01N 2021/3133* (2013.01); *G01N 2201/0231* (2013.01)

(58) Field of Classification Search
CPC . G01J 2003/2869; G01N 21/01; G01N 21/88; G01N 2021/8405; C02F 2209/00; C02F 2209/003; C02F 2209/005; C02F 2209/006
See application file for complete search history.

(56) References Cited

U.S. PATENT DOCUMENTS

| | | | |
|---|---|---|---|
| 3,956,094 A | 11/1976 | Italo | |
| 4,171,256 A | 10/1979 | Themy | |
| 4,328,084 A | 5/1982 | Shindell | |
| 4,472,256 A | 9/1984 | Hilbig | |
| 4,508,687 A | 6/1985 | Houghton | |
| 4,550,011 A | 10/1985 | Roy et al. | |
| 4,599,159 A | 9/1986 | Hilbig | |
| 4,613,415 A | 9/1986 | Wreath et al. | |
| 4,752,740 A | 6/1988 | Steininger | |
| 4,767,511 A | 8/1988 | Aragon | |
| 4,997,540 A * | 3/1991 | Howlett | C02F 1/4674 |
| | | | 204/271 |
| 5,034,110 A | 7/1991 | Glore et al. | |
| 5,039,492 A | 8/1991 | Saaski et al. | |
| 5,221,444 A | 6/1993 | Silveri | |
| 5,228,964 A | 7/1993 | Middleby | |
| 5,240,228 A | 8/1993 | Silveri | |
| 5,252,060 A | 10/1993 | McKinnon et al. | |
| 5,254,226 A | 10/1993 | Williams et al. | |
| 5,279,748 A | 1/1994 | Hackett | |
| 5,401,373 A | 3/1995 | Silveri | |
| 5,468,360 A | 11/1995 | David et al. | |
| 5,545,310 A | 8/1996 | Silveri | |
| 5,603,843 A | 2/1997 | Snee | |
| 5,676,805 A | 10/1997 | Silveri | |
| 5,710,409 A | 1/1998 | Schwarzbacker et al. | |
| 5,752,282 A | 5/1998 | Silveri | |
| 5,759,384 A | 6/1998 | Silveri | |
| 5,885,426 A | 3/1999 | Silveri | |
| 5,930,852 A | 8/1999 | Gravatt et al. | |
| RE36,402 E | 11/1999 | Williams et al. | |
| 5,980,727 A | 11/1999 | Putz et al. | |
| 5,985,155 A | 11/1999 | Maitland | |
| 6,007,693 A | 12/1999 | Silveri | |
| 6,059,942 A | 5/2000 | Barnes et al. | |
| 6,086,746 A | 7/2000 | Nalepa | |
| 6,113,779 A | 9/2000 | Snee | |
| 6,129,850 A | 10/2000 | Martin et al. | |
| 6,200,108 B1 | 3/2001 | Caudil et al. | |
| 6,238,555 B1 | 5/2001 | Silveri et al. | |
| 6,270,680 B1 | 8/2001 | Silveri et al. | |
| 6,277,288 B1 | 8/2001 | Gargas | |
| 6,309,538 B1 | 10/2001 | Khan | |
| 6,331,279 B1 | 12/2001 | Martin | |
| 6,340,431 B2 | 1/2002 | Khan | |
| 6,355,913 B1 | 3/2002 | Authier et al. | |
| 6,372,148 B1 | 4/2002 | Martin et al. | |
| 6,409,926 B1 | 6/2002 | Martin | |
| 6,423,234 B1 | 7/2002 | Martin | |
| 6,476,363 B1 | 11/2002 | Authier et al. | |
| 6,488,408 B1 | 12/2002 | Laflamme et al. | |
| 6,500,332 B2 | 12/2002 | Martin et al. | |
| 6,517,713 B2 | 2/2003 | Gargas | |
| 6,562,243 B2 | 5/2003 | Sherman | |
| 6,627,053 B2 | 9/2003 | Hirota et al. | |
| 6,627,073 B2 | 9/2003 | Hirota et al. | |
| 6,699,381 B2 | 3/2004 | Nakamura et al. | |
| 6,699,441 B2 | 4/2004 | Martin | |
| 6,716,359 B1 | 4/2004 | Dennis, II | |
| 6,717,050 B2 | 4/2004 | Laflamme et al. | |
| 6,740,225 B2 | 5/2004 | Gurry et al. | |
| 6,744,223 B2 | 6/2004 | Laflamme et al. | |
| 6,753,186 B2 | 6/2004 | Moskoff | |
| 6,776,926 B2 | 8/2004 | Martin | |
| 6,782,309 B2 | 8/2004 | Laflamme et al. | |
| 6,813,575 B2 | 11/2004 | Laflamme | |
| 6,814,877 B2 | 11/2004 | Gargas | |
| 6,821,398 B2 | 11/2004 | Von Broemsben | |
| 6,827,847 B1 | 12/2004 | Chauvier | |
| 6,874,175 B2 | 4/2005 | Laflamme et al. | |
| 6,900,736 B2 | 5/2005 | Crumb | |
| 6,913,684 B1 | 7/2005 | Barak et al. | |
| 6,929,516 B2 | 8/2005 | Brochu et al. | |
| 6,942,354 B2 | 9/2005 | Metayer et al. | |
| 6,984,295 B2 | 1/2006 | Shiue et al. | |
| 6,991,735 B2 | 1/2006 | Martin | |
| 6,992,488 B2 | 1/2006 | Lin | |
| 7,108,781 B2 | 9/2006 | Martin | |
| 7,112,768 B2 | 9/2006 | Brochu et al. | |
| 7,158,909 B2 | 1/2007 | Tarpo et al. | |
| 7,292,898 B2 | 11/2007 | Clark et al. | |
| 7,327,275 B2 | 2/2008 | Brochu et al. | |
| 7,351,331 B2 | 4/2008 | Birkbeck | |
| 7,419,406 B2 | 9/2008 | Brochu et al. | |
| 7,440,820 B2 | 10/2008 | Gougerot et al. | |
| 7,489,986 B1 * | 2/2009 | Laflamme | A61H 33/0087 |
| | | | 340/4.3 |
| 7,593,789 B2 | 9/2009 | Gougerot et al. | |
| 7,619,181 B2 | 11/2009 | Authier | |
| 7,701,679 B2 | 4/2010 | Brochu et al. | |
| 7,843,357 B2 | 11/2010 | Brochu et al. | |
| 7,982,625 B2 | 7/2011 | Brochu et al. | |
| 8,104,110 B2 | 1/2012 | Caudill et al. | |
| 8,164,470 B2 | 4/2012 | Brochu et al. | |
| 8,212,222 B2 | 7/2012 | Shakespeare et al. | |
| 2001/0004962 A1 | 6/2001 | Hirota et al. | |
| 2001/0010296 A1 | 8/2001 | Hirota et al. | |
| 2001/0042692 A1 | 11/2001 | Gurry et al. | |
| 2001/0045380 A1 | 11/2001 | Khan | |
| 2001/0050258 A1 | 12/2001 | Gargas | |
| 2001/0052502 A1 | 12/2001 | Gargas | |
| 2002/0031457 A1 | 3/2002 | Martin | |
| 2002/0035403 A1 | 3/2002 | Clark et al. | |
| 2002/0040876 A1 | 4/2002 | Martin et al. | |
| 2002/0074243 A1 | 6/2002 | Nakamura et al. | |
| 2002/0189954 A1 | 12/2002 | Miyazaki et al. | |
| 2003/0024809 A1 | 2/2003 | Broembsen | |
| 2003/0094421 A1 | 5/2003 | Gargas | |
| 2003/0098419 A1 | 5/2003 | Ji et al. | |
| 2003/0107012 A1 * | 6/2003 | Cassidy | G01N 21/01 |
| | | | 250/573 |
| 2003/0146105 A1 | 8/2003 | Shiue et al. | |
| 2005/0061662 A1 | 3/2005 | Broembsen | |
| 2006/0054567 A1 | 3/2006 | Mousseau | |
| 2006/0097878 A1 | 5/2006 | Von Broembsen | |
| 2006/0219630 A1 * | 10/2006 | Abe | B01D 21/0009 |
| | | | 210/600 |
| 2006/0283808 A1 | 12/2006 | Kadlec et al. | |
| 2006/0283809 A1 | 12/2006 | Kilawee et al. | |
| 2007/0012631 A1 | 1/2007 | Coffey et al. | |

(56) References Cited

U.S. PATENT DOCUMENTS

| | | | |
|---|---|---|---|
| 2008/0093225 | A1 | 4/2008 | Cline et al. |
| 2009/0000944 | A1 | 1/2009 | Marui |
| 2009/0098022 | A1 | 4/2009 | Tokhtuev |
| 2009/0218296 | A1 | 9/2009 | King et al. |
| 2010/0101010 | A1 | 4/2010 | McCague |
| 2011/0253637 | A1 | 10/2011 | McCague |
| 2013/0068631 | A1 | 3/2013 | Brochu et al. |
| 2018/0267007 | A1 | 9/2018 | Laflamme et al. |
| 2018/0364155 | A1* | 12/2018 | Thompson ............. G01N 21/80 |

FOREIGN PATENT DOCUMENTS

| | | |
|---|---|---|
| CA | 2483876 | 4/2009 |
| CA | 2349106 | 10/2009 |
| CA | 2442861 | 12/2009 |
| CA | 2521572 | 12/2009 |
| CA | 2361096 | 3/2011 |
| CA | 2467015 | 7/2011 |
| CA | 2492350 | 11/2011 |
| CA | 2357641 | 1/2012 |
| CA | 2412221 | 1/2012 |
| CA | 2499551 | 5/2012 |
| EP | 0133920 A1 | 3/1985 |
| EP | 0243846 A2 | 11/1987 |
| EP | 0377131 B1 | 7/1990 |
| EP | 0540179 A2 | 5/1993 |
| EP | 0835844 A2 | 4/1998 |
| EP | 1108683 A2 | 6/2001 |
| EP | 1108684 A2 | 6/2001 |
| EP | 1340841 A1 | 9/2003 |
| EP | 1233931 B1 | 7/2005 |
| EP | 1647525 A1 | 4/2006 |
| KR | 20030006427 | 1/2003 |
| WO | WO93/22477 | 11/1993 |
| WO | WO99/24369 | 5/1999 |
| WO | WO00/24991 | 5/2000 |

OTHER PUBLICATIONS

International Search Report dated Jan. 13, 2011 in connection with International Patent Application PCT/CA2010/000775, 4 pages.
International Search Report dated Feb. 2, 2011 in connection with International Patent Application PCT/CA2010/000774, 3 pages.
Written Opinion of the International Searching Authority dated Feb. 2, 2011 in connection with International Patent Application PCT/CA2010/000774, 4 pages.
International Report on Patentability completed on Nov. 28, 2012 in connection with International Patent Application PCT/CA2010/000774, 15 pages.
Examiner's Report dated Mar. 19, 2015 in connection with Canadian Patent Application No. 2,799,960—3 pages.
Non-Final Office Action dated Mar. 12, 2015 in connection with U.S. Appl. No. 13/699,252—19 pages.
Examiner's Report dated Nov. 2, 2015 in connection with Canadian Patent Application No. 2,799,960—3 pages.
Final Office Action dated Oct. 28, 2015 in connection with U.S. Appl. No. 13/699,252—16 pages.
Notice of Allowance dated Mar. 15, 2016 in connections with Canadian Patent Application No. 2,799,960—1 page.
Examiner's Report dated May 12, 2016 in connection with Canadian Patent Application No. 2,799,971—4 pages.
Non-Final Office Action dated Jun. 30, 2016 in connection with U.S. Appl. No. 13/699,252—26 pages.
Examiner's Report dated Oct. 31, 2016 in connection with CA Patent 2,799,971—3 pages.
Sensor Halogen ( prior to Feb. 16, 2017).
Final Office Action dated Feb. 9, 2017 in connection with U.S. Appl. No. 13/699,252—31 pages.
Canadian Patent No. 2,799,960 dated Oct. 11, 2016—99 pages.
Examiner's Report dated Mar. 8, 2017 in connection with Canadian Patent Application No. 2,799,971—3 pages.
Examiner's Report dated Nov. 28, 2017 in connection with Canadian Patent Application No. 2,799,971—3 pages.
Examiner's Report dated May 4, 2018 in connection with Canadian Patent Application No. 2,961,087—3 pages.
Non-Final Office Action dated May 3, 2018 in connection with U.S Appl. No. 13/699,252—27 pages.
Non-final Office Action dated Jul. 12, 2018 in connection with U.S Appl. No. 15/460,394—27 pages.
Examiner's Report dated Oct. 31, 2018 in connection with Canadian Patent Application No. 2,799,971—4 pages.
Notice of Allowance dated Oct. 31, 2018 in connection with U.S. Appl. No. 15/460,394—11 pages.

* cited by examiner

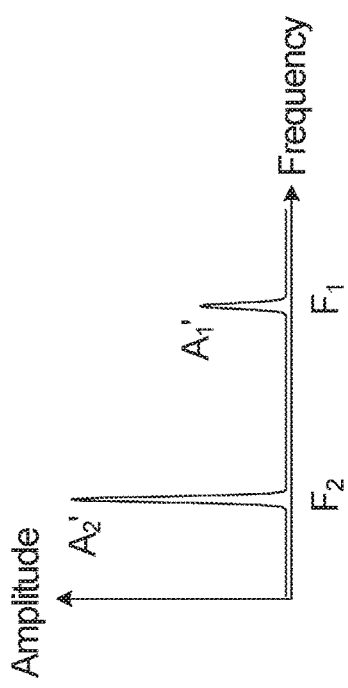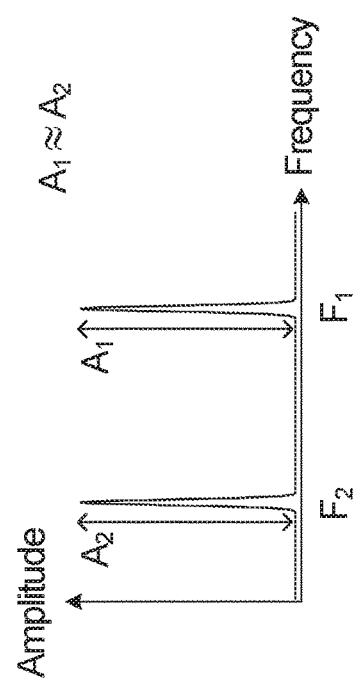

155

| Halogen H | Lower Limit | Upper Limit |
|---|---|---|
| $H_1$ | 3 ppm | 5 ppm |
| $H_2$ | 1 ppm | 3 ppm |
| $H_3$ | 2 ppm | 4 ppm |
| ... | ... | ... |

METHOD, DEVICE AND APPARATUS FOR MONITORING HALOGEN LEVELS IN A BODY OF WATER

CROSS-REFERENCE TO RELATED APPLICATIONS

The present application is a continuation under 35 USC § 120 of co-pending U.S. patent application Ser. No. 15/460,394 filed on Mar. 16, 2017. The contents of the aforementioned document are incorporated herein by reference.

FIELD OF THE INVENTION

The present invention relates generally to the monitoring of halogen levels in bodies of water, and more specifically, to a method, device and system for monitoring halogen levels, including for example monitoring bromine and/or chlorine levels, in a body of water, such as in bathing units (e.g. pools, spas, etc.) and the like.

BACKGROUND

A bathing unit, such as for example a spa or pool, typically includes various components used in the operation of the bathing unit system such as a water holding receptacle, pumps to circulate water in a piping system, a heating module to heat the water, a filter system, an air blower, a lighting system, and a control system for activating and managing the various parameters of the bathing unit components. The circulation system pumps water from the water holding receptacle through the filter system to maintain the body of water at sanitary conditions. In particular, the water passes through the filter system to reduce the accumulation of foreign material, such as hair, soil, or solids, in the pool or spa.

In addition to filtering, bathing unit systems also require regular sanitization in order to maintain hygienic conditions. Allowing sanitation agent levels to either fall below or rise above required levels may result in decreased efficiency of the system. Low levels of chemical sanitizer in the bathing unit can contribute to algae blooms, bacterial breakouts, cloudiness in the water, and chemical imbalances. If left untreated, water-borne bacteria can afflict users of the bathing units with a variety of health problems and illnesses, such as *pseudomonas*, rashes, hot tub lung, ear infections, etc.

Water sanitation is well known and long practiced. Typical sanitation regimens and processes rely on halogen treatment chemicals to provide disinfecting action. Halogens, and in particular free chlorine and bromine, have recently been the chemicals of choice for treating recreational reservoir water.

Conventional halogen-based systems, to be effective, require that the concentration of halogen (chlorine or bromine for example) be maintained within a specified range, which is typically between 3 ppm (parts per million) and 5 ppm. Maintaining a suitable concentration of halogen in the bathing unit typically requires the user to perform periodic measurements for example by using water testing kits and then taking action to adjust the concentration of the sanitation species so that it lies within the desired specified concentration range. Using these measurements, the user may for example add water to reduce the concentration of halogen and/or may cause an action to take place to increase the concentration of halogen (e.g. by controlling an electrolytic cell to increase the generation of halogen). This is a lengthy process which is not always diligently followed by the user, often resulting in less than ideal water conditions.

To address such deficiencies, various automated devices for measuring the concentration of halogen (chlorine or bromine for example) have been proposed.

U.S. Pat. No. 4,752,740 ("the '740 Patent") proposes a water chemistry analysis device for pools, spas, and the like which includes an oxidation-reduction potential (ORP) probe and/or a pH (PH) probe disposed in the recirculation/filtration system. The contents of the aforementioned document are incorporated herein by reference. The ORP probe generates an electrical signal directly related to the active form of a sanitizer contained in the water while the PH probe generates and electrical signal that is related to the acidity/basicity level of the water. The signals are used to display information conveying measured ORP levels against upper and lower limits corresponding to "more than necessary" and "less than necessary" levels of sanitizer in the water and to convey measured PH levels against upper and lower limits corresponding to "lower acidity than optimum" and "higher acidity than optimum" levels of water.

A deficiency associated with devices of the type described in the '740 Patent is that the ORP probe and the PH probe are physical probes that are in contact with the water of the bathing unit. These physical probes are prone to mechanical wear and tear and deposits on the physical probes, which naturally occur in bathing unit environment, often affect the precision of the measurements taken and require frequent calibration.

Another approach that has been proposed more recently, and which may reduce or eliminate the need for physical probes in the water of the receptacle, is to make use of UV spectrometry to measure the concentration of halogen in spas. Generally, the approach includes emitting a light at a specific wavelength through a sample of water and measuring the level of absorption as the light travels through the sample of water. Most chemical compounds absorb light in a manner that varies according to the wavelengths of the light used and the amount of the chemical compound present. The measured level of absorption is used in combination with the spectral signature of the halogen sought to be measured to derive a concentration of the halogen in that sample of water. While in theory such approach may appear simple, in practical bathing unit applications the concentrations of halogen being measured are low and the difference between a suitable concentration of halogen and one that is unsuitable is small. As a result, variations in extraneous factors unrelated to the concentration of the halogen in the water may in some cases materially influence the precision of the measurements obtained rendering them unsuitable for distinguishing between a suitable concentration of halogen and one that is unsuitable.

U.S. Pat. No. 8,212,222 ("the '222 Patent") proposes a method of measuring chlorine concentration in a solution that aims to compensate for a specific one of these extraneous factors, namely the effect of temperature on the precision of the measurements. The contents of the aforementioned document are incorporated herein by reference. More specifically, the '222 Patent proposes a method of measuring chlorine concentration in a solution by making first and second measurements of transmission of ultraviolet light at a selected wavelength through respective first and second samples of the solution held in a "cuvette", where the first and second solution samples are heated to different temperatures. More specifically, the approach proposed by the '222 Patent exploits the variability in the equilibrium point of HOCl/OCl— with temperature and is premised on the absorption spectra of strongly ionised salts, such as nitrates and carbonates dissolved in solution, not changing with temperature. By taking the difference (absolute difference or ratio) from a single wavelength, for example, at 293 nanometers (nm) (the absorption peak of the OCl— species) at two different temperatures, a measurement of the level of OCl— that is less sensitive to water temperature can be derived.

A deficiency with methods and devices of the type described in the '222 Patent is that they require a complex arrangement including a valve arrangement to place sequential samples of the solution in a "cuvette", a heat exchanger to heat one of the samples and not the other, and components for sequentially taking measurements of the samples to obtain two absorption measurements. The complexity of the arrangement proposed in the '222 Patent including the requirement to provide a valve system and a heat exchanger, adds cost to the device. Moreover, the valve arrangement, which includes mechanically moving parts, is prone to mechanical wear and tear, which may reduce the useful life of the arrangement.

Another deficiency with methods and devices of the type described in the '222 Patent is that while the solution proposed may potentially compensate for water temperature effects, the precision of the measurements remains sensitive to other extraneous factors unrelated to the concentration of the halogen. While controlled environments (such as laboratories) may make it possible to achieve suitable levels of precision even at low levels of halogen concentration by eliminating variations of certain extraneous factors, achieving such level of control is not suitable for practical bathing unit environments.

Against the background described above, there is a need in the industry to provide a method, device and system for monitoring halogen levels in bathing units that alleviate at least in part the problems associated with existing methods, devices and systems.

SUMMARY

In accordance with a first general aspect, an apparatus is proposed for monitoring a concentration of a specific halogen in water. The apparatus comprises:
   a. a housing;
   b. an optical absorption analyzer positioned within said housing, said optical absorption analyzer being configured for:
      i. making a first measurement of transmission of ultraviolet light from a light source through a sample of water, said light source emitting light at a specific wavelength, wherein the specific wavelength of the light source is selected at least in part based on the specific halogen whose concentration is being monitored;
      ii. making a second measurement of transmission of ultraviolet light from said light source, wherein the second measurement is taken prior to the ultraviolet light travelling through the sample of water;
      iii. deriving the concentration of the specific halogen at least in part by processing results of the first and the second measurements;
      iv. releasing a signal conveying the derived concentration of the specific halogen.

In accordance with a specific practical implementation, the optical absorption analyzer may comprise a first detector for making the first measurement of transmission of ultraviolet light from the light source through the sample of water and a second detector for making the second measurement of transmission of ultraviolet light from the light source prior to the ultraviolet light travelling through the sample of water. The optical absorption analyzer may also comprise a beam splitter module for directing a first part of ultraviolet light generated by the light source toward the first detector through the sample of water and a second part of ultraviolet light generated by the light source toward the second detector. The optical absorption analyzer may also comprise a processor in communication with the first and second detector configured for deriving the concentration of the specific halogen at least in part by processing the results of the first and the second measurements.

Advantageously, the use of first and second measurements of transmission of ultraviolet light in the proposed apparatus described above to derive the concentration of the specific halogen may allow compensating for effects that may be attributable to variations in the ultraviolet light emitted by light source rather than those that may be attributable to actual concentration of halogen. It is to be appreciated that variations in the ultraviolet light emitted by light source may be due, for example but without being limited to, the variations that occurred in the manufacturing of the light source as well as variations that occur over time as the light source ages.

Optionally, in some implementations, the apparatus may further comprise a temperature sensor for generating a signal conveying water temperature information for the sample of water. In such implementations, the optical absorption analyzer may be configured for deriving the concentration of the specific halogen at least in part by processing the results of the first and the second measurements and the water temperature information. Advantageously, the use of the water temperature information in the proposed apparatus described above to derive the concentration of the specific halogen may allow compensating for effects that may be attributable to variations in water temperature rather than those that may be attributable to actual concentration of halogen.

In some specific practical implementations, the apparatus may be configured for monitoring a specific halogen amongst different halogen types by using a light source suitable for the specific halogen. Halogen types frequently used in bathing units for example may include chlorine and bromine.

For example, in some specific applications in which the specific halogen whose concentration is being monitored is bromine, the specific wavelength at which the light source used emits light is between 280 nm and 380 nm. In some specific implementations, the specific wavelength at which the light source used emits light may be between 300 nm and 360 nm. In a non-limiting practical implementation, the specific wavelength at which the light source used emits light is about 310 nm. In another non-limiting practical implementation, the specific wavelength at which the light source used emits light is about 330 nm.

In some implementations, the light source may be a first light source emitting light at a first specific wavelength. The optical absorption analyzer may further be configured for making a first measurement of transmission of light from a second light source through the sample of water, the second light source emitting light at a second specific wavelength different from the first specific wavelength. The optical absorption analyzer may also be configured for making a second measurement of transmission of light from the second light source, wherein the second measurement is taken prior to the light from the second light source travelling through the sample of water. The optical absorption analyzer is configured to derive the concentration of the specific halogen by processing at least results of the first and the second measurements of transmission of light from the second light source and the results of the first and the second measurements of transmission of light from the first light source.

In some specific practical implementations, the same detector may be used for making the first measurements of transmission of light from the first and second light sources through the sample of water and the same second detector may be used for making the second measurements of transmission of light from the first and second light sources prior to the light travelling through the sample of water. In addition, the same beam splitter module as that used from the first light source may be used for directing a first part of light generated by the second light source toward the first detector through the sample of water and a second part of light generated by the second light source toward the second detector.

In some specific practical implementations, the second light source emits light at a wavelength that is generally unaffected by the concentration of the halogen in the sample of water. In a non-limiting implementation, the second light source transmits at a wavelength that is in the visible range of the spectrum. For example, the second specific wavelength at which the second light source emits light may be between about 450 nm and 1100 nm. In some specific implementations, the second specific wavelength at which the second light source emits light is between about 475 nm and 550 nm. In a non-limiting practical implementation, the second specific wavelength at which the second light source emits light is about 500 nm.

Advantageously, the use of measurements of transmission of ultraviolet light of first and second light sources emitted lights at different wavelengths in the proposed apparatus described above may allow compensating for effects that may be attributable to impurities in an optical path between the first light source and the first detector rather than those that may be attributable to actual concentration of the halogen in the sample of water. It is to be appreciated that impurities in the optical path between the first light source and the first detector may be due to, for example but without being limited to, sand particles in the sample of water and/or particles having adhered to walls of a cuvette between the first light source and the first detector wherein the cuvette holds the sample of water.

In some specific practical applications, the first and second light sources may be sequentially turned "ON" and "OFF", wherein the light source emits light when it is "ON" and does not emit light when it is "OFF", so that in turn measurements may be made by the detectors. Alternatively, the first and second light sources may be continuously left "ON" and may be operated according to an intermittent light pattern, such as for example, but without being limited to, sinusoidal light patterns.

Advantageously, keeping the first and second light sources "ON" and operating them according to an intermittent (e.g., a periodic) light pattern may present a number of advantages including reducing transition effects caused by activating the light sources.

In a specific practical application, the first light source emits light at a first frequency and the second light source emits light at a second frequency, wherein the first frequency is different from the second frequency. The optical absorption analyzer of the apparatus is configured for deriving the concentration of the specific halogen at least in part based on a frequency distribution associated with:
  the results of the first and the second measurements of the transmission of light from the first light source; and
  the results of the first and the second measurements of the transmission of light from the second light source.

In some specific practical applications, the first and second frequencies may be chosen so that they are not harmonics of one another. In a specific non-limiting example of implementation, the first light source may have a first frequency between 420 and 580 Hz, such as for example about 450 Hz. The second light source may have a second frequency above 350 Hz such as for example about 570 Hz.

Advantageously, by selecting certain first and second frequencies, the effects of external interferences may be reduced on the measurements of the transmission of light from the first and second light sources. External interferences may include, for example but without being limited to, changes in ambient light (for example due to the time of day, the amount of sun, the type of light, clouds, etc.) as well as the presence of electromagnetic (EM) fields (typically caused by the electrical grid emitting EM fields at 60 Hz, 120 Hz and harmonics (240 Hz, 480 Hz, etc.)). In a specific example, the first and second frequencies of the light sources may be chosen to be sufficiently high so that a high pass filter can be used to filter out effects of changes in ambient light, which would typically be at relatively low frequencies. In addition, a suitable filter, such as a band-pass filter, may be used to filter out effects of the electrical/electronic signals without hindering the first and second frequencies of the first and second light sources. In such cases, the first and second frequencies of the light sources may be chosen not to correspond to a harmonic of the electrical/electronic signals.

In some specific implementations, the housing of the apparatus may have walls at least partially made of a material permeable to ultraviolet light defining opposing windows for allowing transmission of ultraviolet through the sample of water from a light source to a detector. Any suitable material may be used such as, for example but without being limited to, quartz and/or suitable types of optical glass.

In specific practical implementations of the apparatus, the housing may have different configurations.

In specific implementations of a first type, the housing is configured to be connected to circulation piping of a bathing unit including at least one circulation pump. When the housing is connected to the circulation piping of the bathing unit, the housing is in fluid communication with the circulation piping so that water from a receptacle of the bathing unit is circulated through a space within the housing.

In specific implementations of a second type, the housing is a free-standing device configured to float on top of the water held in a receptacle of a bathing unit. The housing may have a lower portion configured for being at least partially submerged in water during use and an upper portion configured for extending at least partially above the level of the water in the bathing unit during use. The lower portion includes walls extending into the water and defining spaced apart opposing windows made at least in part of a material permeable to ultraviolet light, the sample of water being between the spaced apart opposing windows. Optionally, the upper portion of the housing may include a user interface device, including but not limited to a display screen, in electronic communication with the optical absorption analyzer for displaying information derived from the derived concentration of the specific halogen.

Optionally, the apparatus may comprise an antenna for transmitting a signal conveying the derived concentration of the specific halogen to a remote device, such as a smart phone, computing device and/or bathing unit controller for example. The remote device may include a processing unit and a display for conveying the derived concentration of the specific halogen and/or for processing the derived concentration of the specific halogen to derive control signals for controlling the operations of one or more devices in order to adjust the concentration of halogen in the bathing unit. In a non-limiting example, the control signals are configured for controlling operation of an electrolytic cell to adjust the amount of halogen being generated. Alternatively, or in addition, the control signals may be configured for controlling operation of one or more valves for adding water to the bathing unit to reduce the concentration of halogen.

In accordance with another aspect, a method is provided for monitoring a concentration of a specific halogen in water. The method comprises:

- making a first measurement of transmission of ultraviolet light from a light source through a sample of water, said light source emitting light at a specific wavelength, wherein the specific wavelength of the light source is selected at least in part based on the specific halogen whose concentration is being monitored;
- making a second measurement of transmission of ultraviolet light from said light source, wherein the second measurement is taken prior to the ultraviolet light travelling through the sample of water;
- deriving the concentration of the specific halogen at least in part by processing results of the first and the second measurements;
- releasing a signal conveying the derived concentration of the specific halogen.

In some specific implementations, the method may also comprise generating a signal conveying water temperature information for the sample of water and deriving the concentration of the specific halogen at least in part by processing the results of the first and the second measurements and the water temperature information.

In some specific implementations, the light source may be a first light source and the specific wavelength may be a first specific wavelength, and the method may further comprise:

a. making a first measurement of transmission of light from a second light source through the sample of water, said second light source emitting light at a second specific wavelength, wherein the second specific wavelength is different from the first specific wavelength;
b. making a second measurement of transmission of light from said second light source, wherein the second measurement is taken prior to the light travelling through the sample of water;
  wherein the concentration of the specific halogen is derived by processing at least:
    i. results of the first and the second measurements of transmission of light from said second light source; and
    ii. the results of the first and the second measurements of transmission of light from said first light source.

Optionally, the first light source may emit light at a first frequency and the second light source may emit light at a second frequency, wherein the first frequency is different from the second frequency. The method may comprise deriving the concentration of the specific halogen at least in part based on a frequency distribution associated with:

a. the results of the first and the second measurements of the transmission of light from said first light source; and
b. the results of the first and the second measurements of the transmission of light from said second light source.

Optionally still, the method may comprise transmitting a signal conveying the derived concentration of the specific halogen to a remote device, the remote device including a display for conveying the derived concentration of the specific halogen. Alternatively, or in addition, the method may comprise transmitting the signal conveying the derived concentration of the specific halogen to a processing module configured for using the derived concentration of the specific halogen to control generation of specific halogen for a bathing unit.

In accordance with another aspect, a device for monitoring a concentration of a specific halogen in a bathing unit is provided. The device comprises a housing configured for floating atop a body of water held in a receptacle of the bathing unit, the housing having a lower portion configured for being at least partially submerged in water during use and an upper portion configured for extending at least partially above the water, the lower portion including walls extending into the body of water and defining spaced apart opposing windows made at least in part of a material permeable to ultraviolet light. The device also comprises an optical absorption analyzer positioned within the housing. The optical absorption analyzer is configured for making a measurement of transmission of ultraviolet light from a light source through a sample of water between the spaced apart opposing windows, the light source emitting light at a specific wavelength, wherein the specific wavelength of the light source is selected at least in part based on the specific halogen whose concentration is being monitored. The optical absorption analyzer is also configured for deriving the concentration of the specific halogen at least in part by processing results of the measurements of transmission of ultraviolet light from a light source through the sample of water and for releasing a signal conveying the derived concentration of the specific halogen.

All features of embodiments which are described in this disclosure and are not mutually exclusive can be combined with one another. Elements of one embodiment can be utilized in the other embodiments without further mention.

Other aspects and features of the present invention will become apparent to those ordinarily skilled in the art upon review of the following description of specific embodiments in conjunction with the accompanying drawings.

BRIEF DESCRIPTION OF THE DRAWINGS

A detailed description of the embodiments of the present invention is provided herein below, by way of example only, with reference to the accompanying drawings, in which:

FIGS. 12A and 12B show graph of a frequency domain representation of light signals received at detector of the device of FIG. 9 and implemented in accordance with the variant depicted in FIG. 11;

It will be noted that throughout the appended drawings, like features are identified by like reference numerals.

Figure 1:
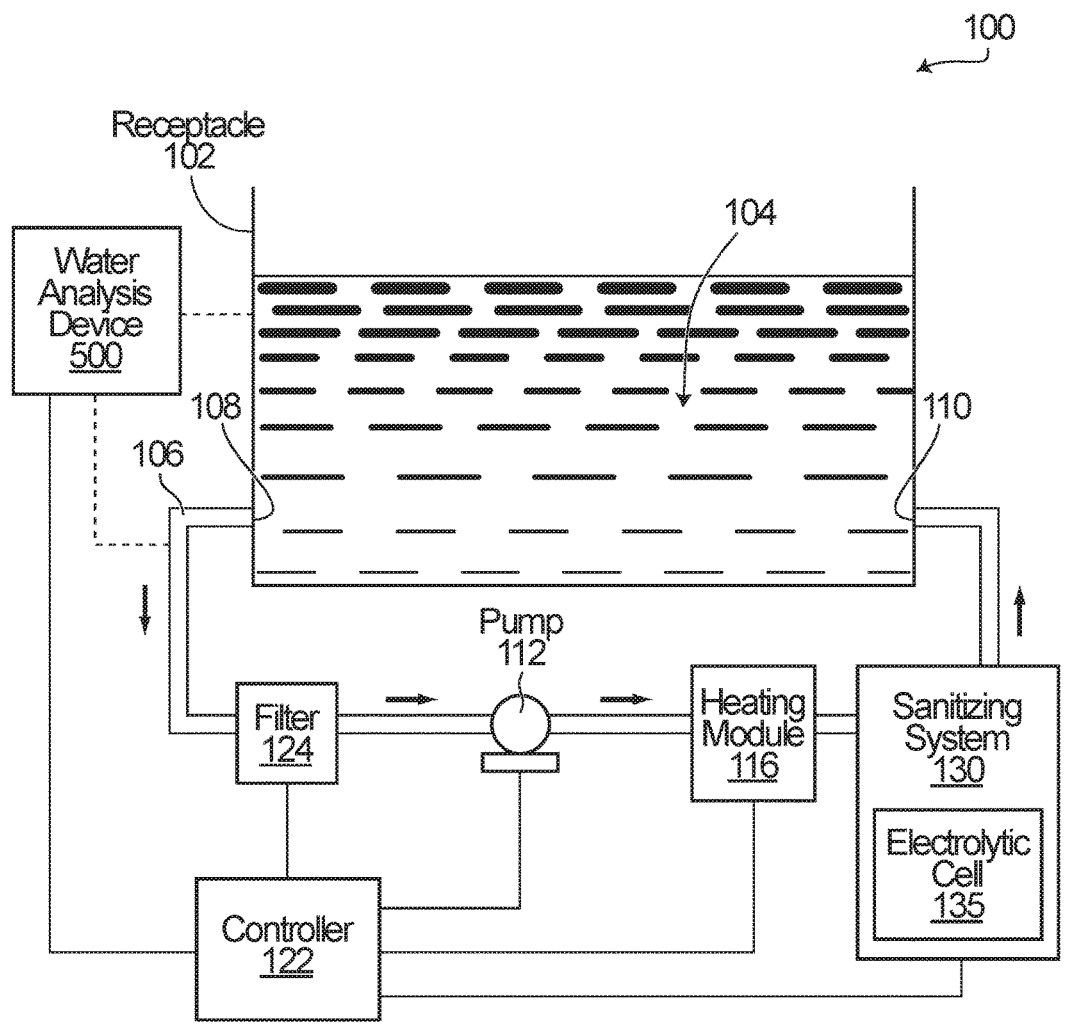
FIG. 1 is a diagram of a bathing unit system incorporating a water analysis device for monitoring a concentration of a specific halogen in water in accordance with a specific example of implementation.

In the drawings, the embodiments of the invention are illustrated by way of examples. It is to be expressly understood that the description and drawings are only for the purpose of illustration and are an aid for understanding. They are not intended to be a definition of the limits of the invention.

DETAILED DESCRIPTION

The description below is directed to specific implementations and uses of embodiments of the invention in the context of bathing units. It is to be understood that the term "bathing unit", as used for the purposes of the present description, refers to spas/swim-spas, whirlpools, hot tubs, bath tubs, therapeutic baths and swimming pools and any other type of unit having a water receptacle holding water in which a halogen has been dissolved. Moreover, it is to be appreciated that while specific embodiments of the invention have been described for using in the context of bathing units, the person skilled in the art will appreciate in view of the present description that alterative embodiments may be configured for use in an environment including a body of water other than a bathing unit in which measurement of a concentration of halogen may be of interest.

FIG. 1 illustrates a block diagram of a bathing unit system 100 incorporating a water analysis device 500 in accordance with a specific example of implementation. The bathing unit system 100 includes a bathing unit receptacle 102 for holding water 104, water inlets 110 (only one is shown) which will typically be connected to respective jets, water outlets 108 (only one is shown) and a circulation system 106 including a flow conduit for removing and returning water from and to the receptacle 102 through the water inlets and water outlets. The circulation system 106 depicted is shown as having a single flow conduit for the purpose of simplicity, however, the person skilled in the art will appreciate that practical implementations of the bathing unit system 100 may include multiple flow conduits interconnecting water inlets and water outlets of the receptacle 102. A heating module 116, a water pump 112 and a filter 124 are shown positioned within the circulation system 106. It should be understood that the bathing unit 100 may include more or fewer bathing unit components that may be positioned in various suitable positions in the circulation system. The bathing unit system 100 may further include a sanitizing system 130 for sanitizing the water 104 in the receptacle 102. In some embodiments, the sanitizing system 130 may comprise an electrolytic cell 135 configured to release a free halogen in the water of the bathing unit 100.

A bathing unit controller 122 controls the settings of the components of the bathing unit system 100 including the settings of the heating module 116, the water pump 112, the filter 124 and/or the sanitizing system 130. The controller 122 receives electrical power from an electric power source (not shown) and controls the distribution of power supplied to the various bathing unit components on the basis of control signals originating from various sensors, program instructions and/or user commands in order to cause desired operational settings to be implemented. Some manners in which the bathing unit controller 122 may be configured and used to control the bathing unit components for the regulation of the operation of the bathing unit system 100 are generally known in the art and are not critical to the invention and as such will not be described in further detail here.

As depicted in FIG. 1, a water analysis device 500 may be used in connection with the bathing unit system 100. More specifically, the water analysis device 500 is configured to monitor a concentration of a specific halogen H in the water of the bathing unit system 100 to assist in maintaining such concentration within a desired operational range. To that end, the water analysis device 500 comprises an optical absorption analyzer 150 and a housing 502 within which the optical absorption analyzer 150 is disposed. The halogen H whose concentration is monitored may be any suitable halogen. For instance, in this embodiment, the halogen H is bromine. However, in other embodiments, the specific halogen H may be chlorine or any other suitable halogen. It is noted that in this description, the term "halogen" may also refer to chemical species containing halogens rather than pure elements, for instance hypochlorous and/or hypobromous acid.

The water analysis device 500 may be embodied in different types of configurations.

"Standalone" Configuration of Water Analysis Device 500

Figure 2A:
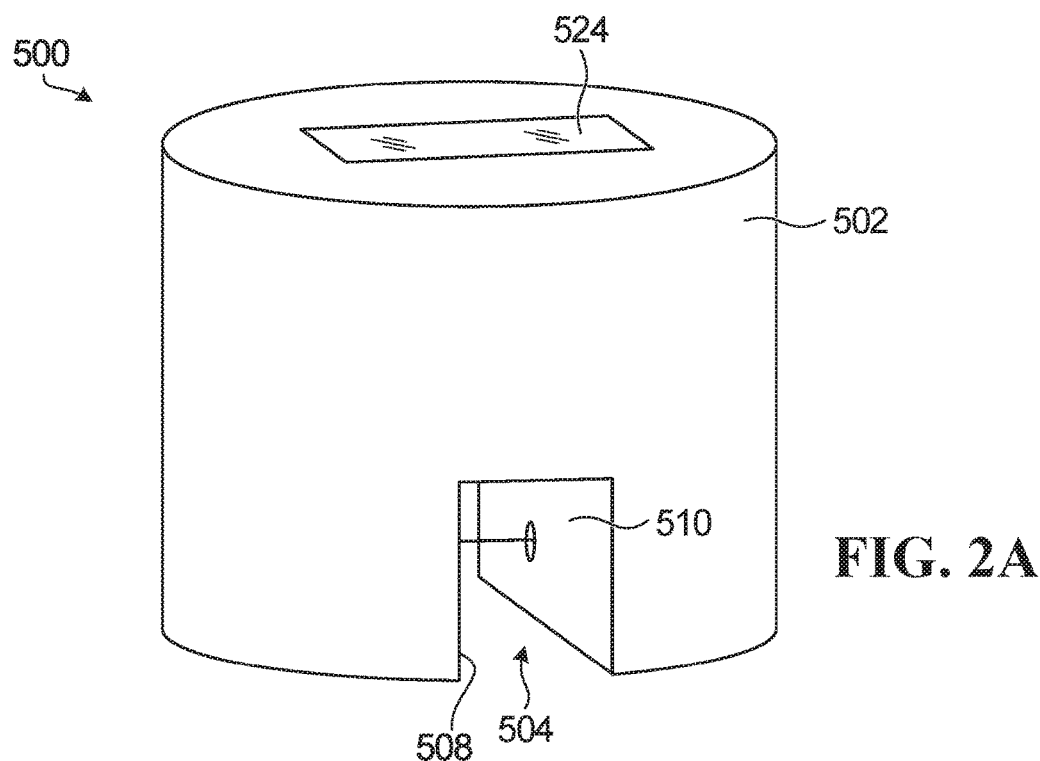
FIGS. 2A and 2B are diagrams of a water analysis device suitable for use in a bathing unit system of the type shown in FIG. 1, wherein the water analysis device is configured in accordance with a free-standing type of implementation.
Figure 2B:
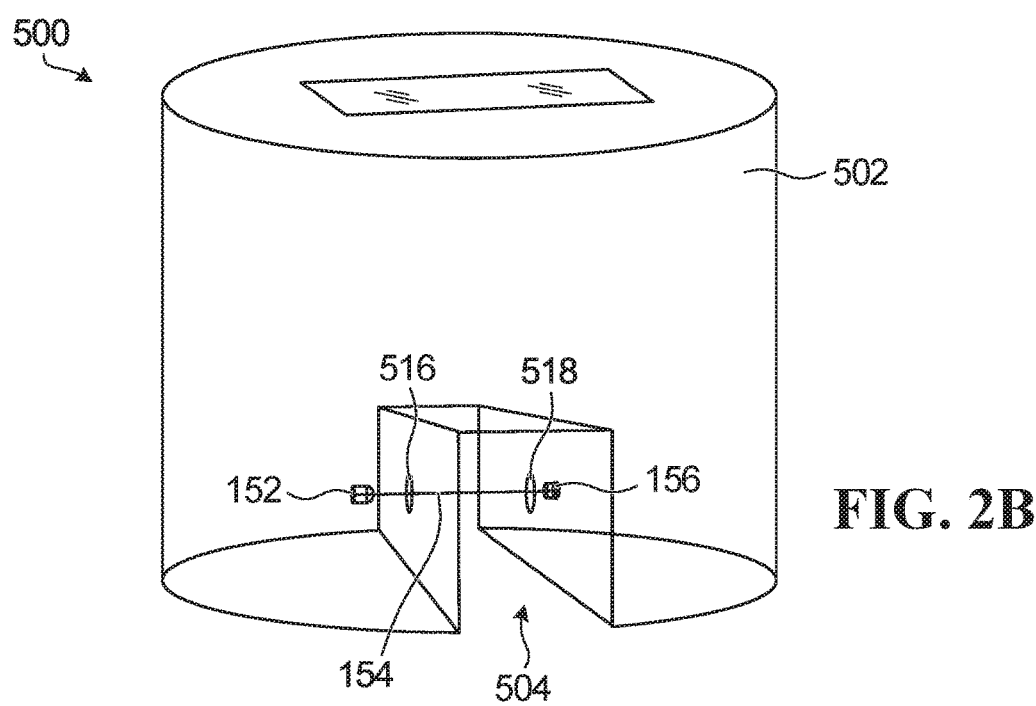
Figure 3:
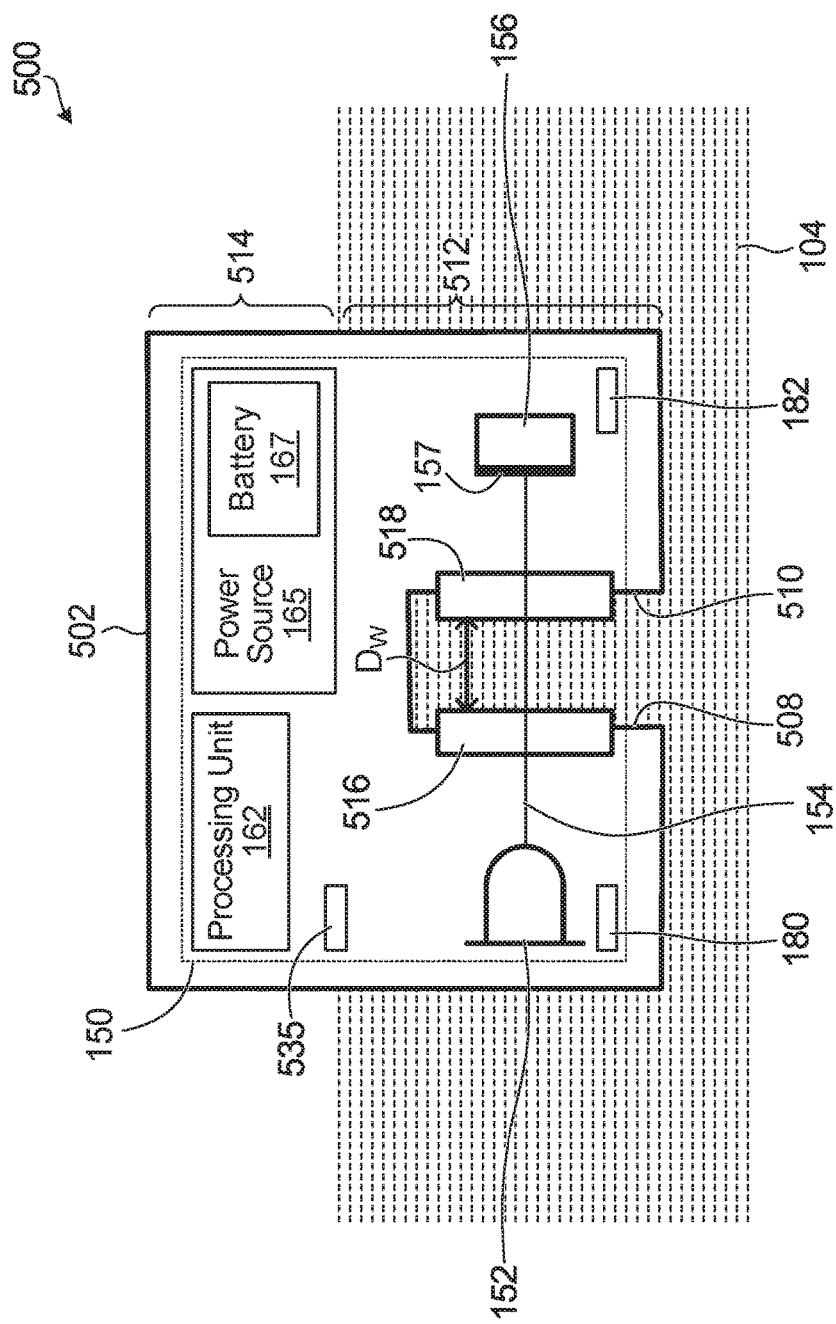
FIG. 3 shows a water analysis device of the type shown in FIGS. 2A and 2B positioned to float on a body of water, the device including an optical absorption analyzer in accordance with a first specific implementation.

In a first type of configuration, shown in FIGS. 2A, 2B and 3, the water analysis device 500 is a standalone device configured to be disposed in the water 104 contained in the receptacle 102 of the bathing unit system 100 of FIG. 1. The water analysis device 500 is a "standalone" device in that it is structurally separate from the other components of the bathing unit 100 (e.g., the circulation system 106). More specifically, in this embodiment, the housing 502 is configured to float atop the water 104 held in the receptacle 102 such that an upper part of the housing 502 remains above a level of the water 104 and a lower part of the device is submersed below the water level when the analysis device 500 is disposed in the receptacle 102. In this specific example of implementation, the housing 502 comprises a lower portion 512 configured for being at least partially submerged in water during use and an upper portion 514 configured for extending at least partially above the water 104 held in the receptacle 102 during use. This may be achieved for example by ensuring that the housing 502 has a density that is less than a density of the water 104 in the receptacle.

The lower portion 512 of the housing 502 comprises a pair of opposing walls 508 510 which in use extend into the water 104 of the receptacle and which define a space 504 there between where water can circulate. The walls 508 510 include opposing windows 516 518 spaced apart by a distance $D_W$ and which are made of a material permeable to ultraviolet light such as, for example, quartz, suitable types of optical glass, plastic (e.g., cellulose diacetate, polyethylene, acrylic, polyester, etc.) or any other suitable material.

Figure 15A:
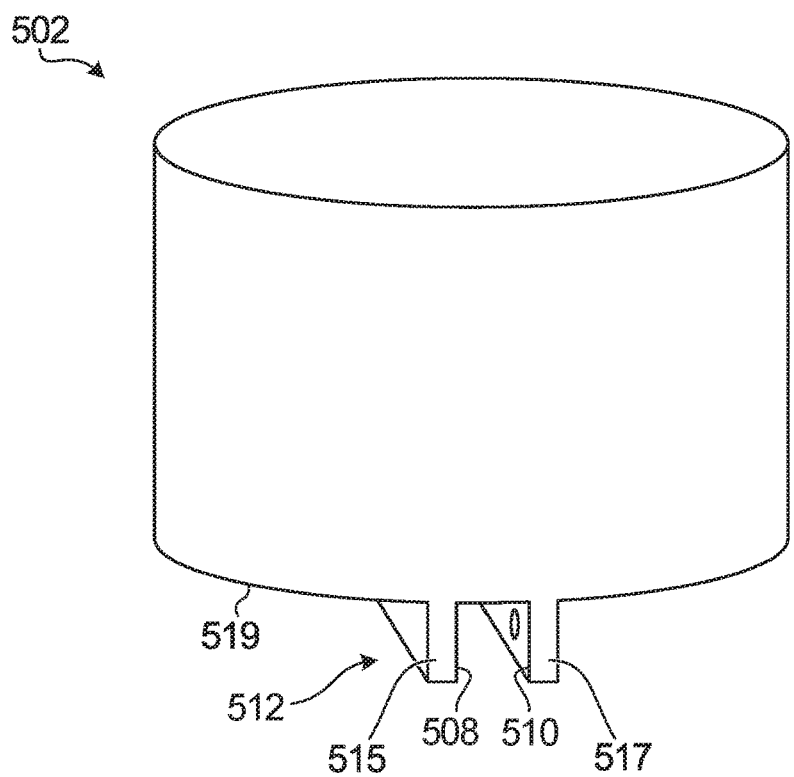
FIGS. 15A and 15B show different examples of shapes of a space in a lower portion of a housing of the device of FIG. 3 in which a sample of water is received.
Figure 15B:
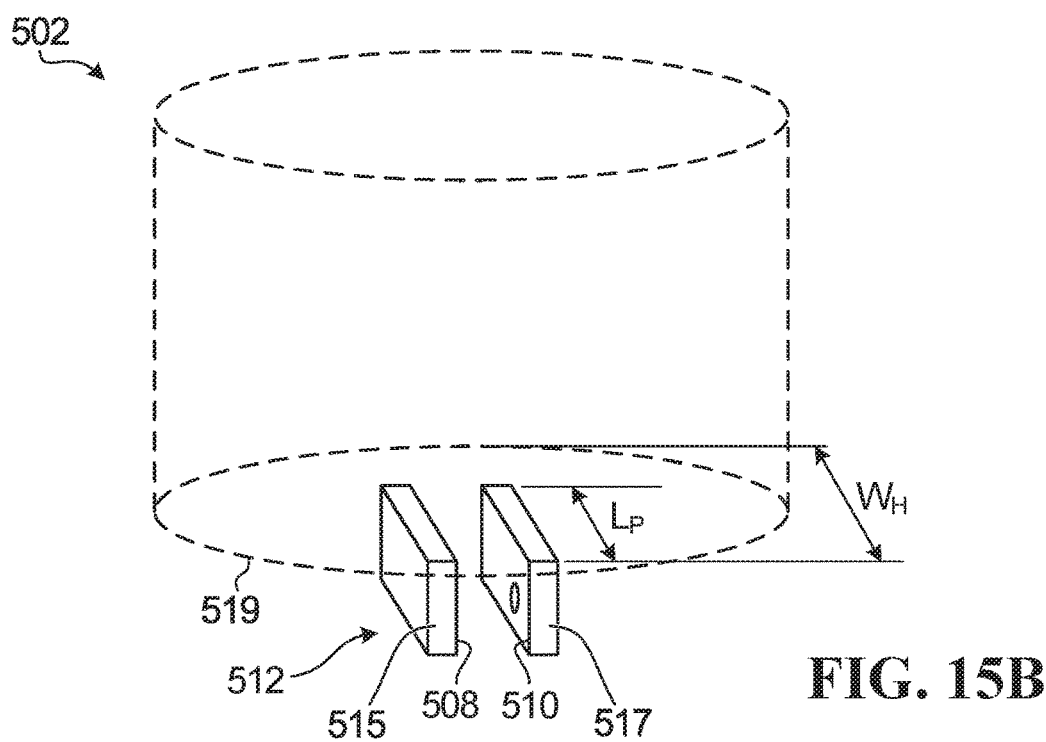

In the specific example of implementation depicted in FIGS. 2A 2B and 3, the housing 502 is configured such that the space 504 of the lower portion 512 of the housing 502 is substantially U-shaped. However, the space 504 defined by the walls 508 510 of the housing 502 may be shaped differently in other examples. For instance, in other examples, the space 504 defined by the walls 508, 510 may be V-shaped, cylindrical, or may have any other suitable shape. FIGS. 15A and 15B show yet other non-limiting configurations that may be formed by the walls 508 510 of the housing 502. For instance, FIG. 15A shows a specific example of implementation in which the lower portion 512 of the housing 502 comprises a pair of projections 515 517 projecting from a bottom surface 519 of the housing 502 and which define the walls 508 510. In this example, the projections 515 517 extend longitudinally along a substantial portion of a width $W_H$ of the housing 502. Notably, the projections 515 517 extend substantially from one side of a periphery of the housing 502 to an opposite side of the periphery of the housing 502. FIG. 15B shows another specific example of implementation in which the projections 515 517 extend longitudinally along a limited portion of the width $W_H$ of the housing 502. For example, in some cases, a ratio of a length $L_P$ of each projection 515 517 over the width $W_H$ of the housing 502 may be no more than 80%, in some cases no more than 70%, in some cases no more than 50%, and in some cases even less. The projections 515 517 may contain components of the optical absorption analyzer 150, including but not limited to the light source 152 and the detector 156.

While the embodiment depicted in FIG. 3 shows a standalone device configured to float on the water 104, in alternative implementations (not shown in the figures) the standalone device may be entirely submerged in the water during use (e.g., by being anchored to a structure of the receptacle 102 or by having a sufficiently high density). In such cases, both the lower and upper portions 512, 514 of the housing 502 may be submerged in the water. In some cases, the water analysis device 500 may even be configured to be disposed at a bottom of the receptacle 102.

Figure 13:
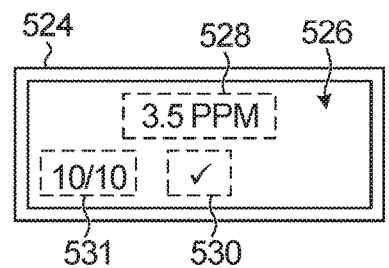
FIG. 13 shows a simplified representation of a user interface device of the device of FIG. 3 in accordance with a non-limiting example of implementation.

Optionally, with reference to FIGS. 2A and 13, the upper portion 514 of the housing 502 may comprise a user interface device 524 configured for outputting information to a user and, in some cases, receiving inputs from the user. For instance, in the example of implementation depicted in FIG. 13, the user interface device 524 is configured to display information related to results obtained by the optical absorption analyzer 150. To that end, the user interface device 524 comprises a display 526 (e.g., a screen) which may convey one or more information elements related to results obtained by the optical absorption analyzer 150 related to a concentration of a specific halogen in the water. In some implementations, the user interface device 524 may comprise user data entry module 527 for receiving inputs from the user (shown schematically in FIG. 10) which may comprise user operable controls such as a keyboard, key pads, buttons, touch sensitive screen or any other suitable form of user data entry device. In some cases, the data entry module 527 may be integrated within the display, for example in cases where the display 526 is a touch screen display.

The water analysis device 500 may also comprise a power source 165 for powering the various components of the water analysis device 500, including the optical absorption analyzer 150. This may be particularly useful in embodiments in which the water analysis device 500 is a standalone device. In the embodiment depicted in FIG. 3, the power source 165 is shown as comprising a battery 167 (e.g., a lithium-ion battery). In a variant shown in FIG. 17, the power source 165 of the water analysis device 500 may comprise a solar panel 600 for recharging the battery 167. More specifically, in accordance with a specific example of implementation, the solar panel 600 may be disposed on part of the upper portion 514 of the housing 500 to receive sunlight which may be converted into an electrical input for the battery 167 of the power source 165. It is to be appreciated that while examples of power sources 165 for the water analysis device 500 have been described, many other suitable ways for providing power to the water analysis device 500 may be contemplated, including for example through a connection to standard wiring, directly or through the bathing unit controller 122 (shown in FIG. 1).

"In-Line" Configuration of Water Analysis Device 500

Figure 6:
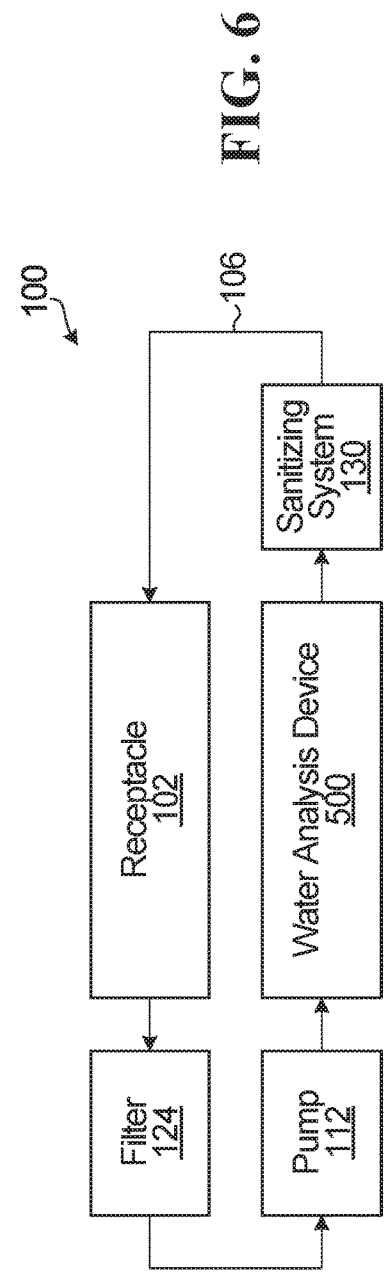
FIG. 6 shows a functional block diagram of a bathing unit system including a water circulation path in which a water analysis device of the type shown in FIG. 4 has been positioned in-line in accordance with a non-limiting implementation of the invention.
Figure 18:
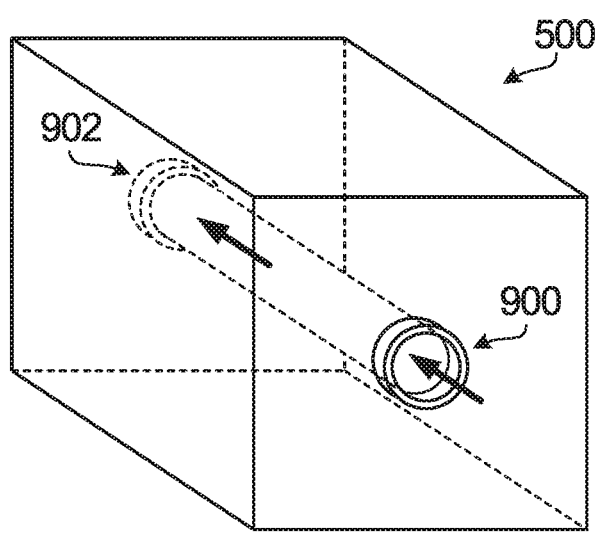
FIG. 18 shows a non-limiting example of a physical embodiment of the water analysis device of FIGS. 4, 7, 8 and 9.

In a second type of configuration, shown in FIGS. 4, 6, 7, 8 and 9, the water analysis device 500 may be integrated within a circulation system 106 of the bathing unit system 100 along with one or more other components of the bathing unit 100, as shown for example in FIG. 6. More specifically, in such second type of configuration, the housing 502 of the water analysis device 500 may include a chamber forming a space 504 for holding a sample of water, wherein the chamber is in fluid communication with circulation piping 164 of the circulation system 106 of the bathing unit 100 such that water from the receptacle 102 is circulated through the space 504, notably via an inlet 900 of the water analysis device 500 through which water enters the space 504 and an outlet 902 of the water analysis device 500 through which water exits the space 504, as shown in FIG. 18. The chamber may be generally tubular in shape and includes walls 508 510 having opposing windows 516 518 made of a material permeable to ultraviolet light such as, for example, quartz, suitable types of optical glass or any other suitable material.

Now that we have described some examples of physical configurations of the water analysis device 500, we will now describe some different manners in which this device operates to monitor halogen levels in water, include some different configurations of the optical absorption analyzer 150. It is to be appreciated that the while various examples of the optical absorption analyzer 150 may be described with reference to either the standalone configuration or the in-line configuration of the water analysis device 500, these examples may be used interchangeably with one or the other configurations in alternative implementations.

Optical Absorption Analyzer

As mentioned above, the optical absorption analyzer 150 of the water analysis device 500 is configured to monitor a concentration of one or more specific halogens (H) in the water of the bathing unit 100.

Figure 4:
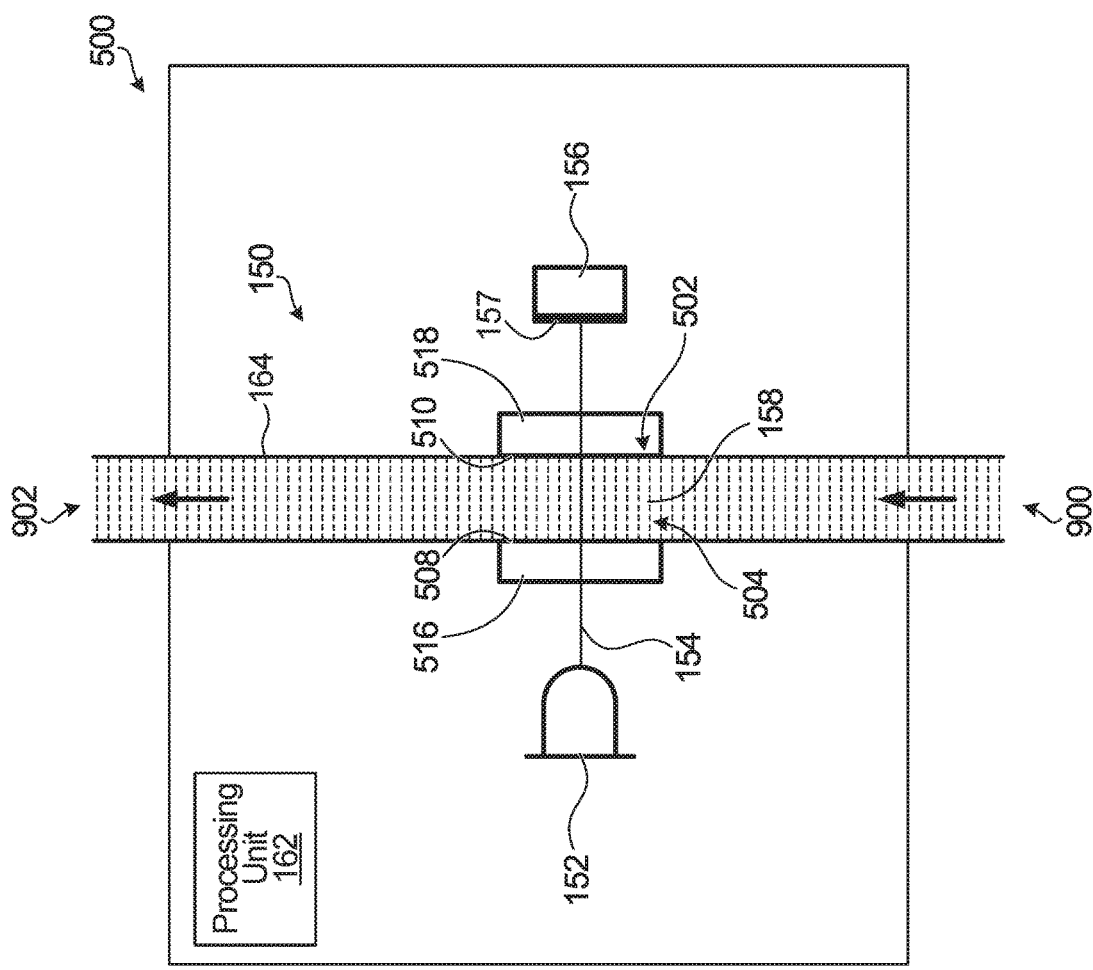
FIG. 4 is a functional block diagram of a water analysis device suitable for use in a bathing unit system of the type shown in FIG. 1, wherein the water analysis device is configured in accordance with an in-line type of implementation and includes an optical absorption analyzer similar to that shown in FIG. 3.

In the embodiment shown in FIGS. 3 and 4, the optical absorption analyzer 150 comprises a (first) light source 152 configured to emit a beam of light 154 and a detector 156. In use, the beam of light 154 emitted by the light source 152 is directed towards a sample of water 158 obtained from water in the bathing unit 100. Specifically, the beam of light 154 travels through the window 516 of the housing 502, through the sample of water 158 contained in the space 504 defined by the housing 502 and through the window 518 of the housing 502. The detector 156 is positioned to receive the beam of light 154 after it has travelled through the sample of water 158 in order to make a measurement of light received from the light source 152. As will be discussed in more detail below, by using a light source 152 emitting light at a selected specific wavelength that is chosen based on a specific halogen H that is of interest, an estimate of the concentration of the halogen H in the water of the bathing unit 100 can be derived from the measurement made by the detector 156.

The light source 152 may comprise any of a variety of types of light-emitting members. In this specific example of implementation, the light source 152 comprises a light-emitting diode (LED). However, the light source 152 may comprise any other type of light-emitting member in other examples, such as an incandescent bulb, a discharge lamp, a laser, or any other suitable type of light-emitting member. As most light-emitting members emit light in a diverging manner (i.e., light rays emitted by the light-emitting member may diverge from one another), the light source 152 may also comprise one or more optical elements (not shown) such as lenses or concave mirrors which are configured to collimate the light rays emitted by the light-emitting member to direct the light rays towards the sample of water 158. In this example, where the light-emitting member is an LED, the optical element of the light source 152 may constitute a plastic body encapsulating the LED and which is domed to collimate the light rays emitted by the LED.

As noted above, the type of light-emitting member comprised by the light source 152 (e.g., incandescent bulb, laser, LED, etc.) may be chosen in accordance with the specific halogen H that is to be monitored by the optical absorption analyzer 150. More specifically, the light-emitting member of the light source 152 is chosen such that a wavelength of the beam of light 154 emitted by the light source 152 is absorbed by the specific halogen H that is of interest. In this example, where the halogen H being monitored is bromine, the wavelength at which the light source 152 emits light would be in the ultraviolet part of the spectrum between 280 nm and 380 nm. In some examples, the wavelength at which the light source 152 emits light may be between 300 nm and 360 nm. In a non-limiting practical implementation, the wavelength at which the light source 152 emits light is about 310 nm. For some non-limiting example of implementations, light source 152 may be implemented by using an off-the-shelf device such as UV LED device model No. UVLED-UV310R50 commercialized by BYTECH Electronics Co., Ltd. however other suitable types of commercially available light sources may be used in other alternative implementations. In accordance with another non-limiting practical implementation, the wavelength at which the light source 152 emits light may be about 330 nm.

The detector 156 is a photodetector configured to sense light. To that end, the detector 156 comprises a light-sensing surface 157 that substantially faces the light source 152 to receive the beam of light 154 emitted by the light source 152. More particularly, the light-sensing surface 157 of the detector 156 converts light photons into current. For instance, in this example, the detector 156 is a photoelectric sensor such as a photodiode. The detector 156 may be any other suitable type of sensor capable of sensing light in other embodiments (e.g., a phototransistor). For some non-limiting example of implementations, detector 156 may be implemented by using by using an off-the-shelf device such as 4.8 mm Semi-Lens Silicon PIN photodiode model No. PD438C/S46 commercialized by Everlight however other suitable types of commercially available photodiodes may be used in other alternative implementations.

The optical absorption analyzer 150 also comprises a processing unit 162 configured to process data related to operation of the optical absorption analyzer 150. For instance, the processing unit 162 is configured to process a signal transmitted to the processing unit 162 by the detector 156. Notably, the signal received by the processing unit 162 from the detector 156 is representative of the measurement of ultraviolet light sensed by the detector 156. In a manner that will be explained in more detail below, the processing unit 162 is programmed for deriving an estimate of the concentration of the halogen H present in the sample of water 158 based at least in part by processing the measurement of ultraviolet light sensed by the detector 156.

The concentration of the halogen H may be derived by Equation 1 (also known as the Beer-Lambert equation) reproduced below:

$$\log\left(\frac{\varphi_e^i}{\varphi_e^t}\right) = \varepsilon c l \quad \text{(Equation 1)}$$

In Equation 1 above, $\varphi_e^i$ is a radiant flux incident on the sample of water 158 and $\varphi_e^t$ is a radiant flux transmitted through the sample of water 158. The molar attenuation coefficient ε is a property of the halogen H while c is a molar concentration of the halogen H in the sample of water 158 under study. Finally l is the optical pathlength of the beam of light 154 (i.e., a distance the beam of light 154 travels from the light source 152 to the detector 156 in the sample of water 158). Thus, using Equation 1, the processing unit 162 can derive the molar concentration c of a specific halogen H in the sample of water 158.

It is noted that the optical pathlength l of the beam of light 154 is determined by the distance $D_W$ between the windows 516, 518. Notably, the optical pathlength l of the beam of light 154 can be optimized by adjusting the distance $D_W$. For instance, if the distance $D_W$ between the windows 516, 518 is made too small, the sample of water 158 may be too small to contain an appreciable concentration of the halogen H. Moreover, if the distance $D_W$ between the windows 516, 518 is made too great, the sample of water 158 may contain too many impurities (e.g., dirt, air bubbles, etc.) which may affect the accuracy of the derived concentration of halogen H.

Optionally, in some embodiments, as shown in FIG. 3, the optical absorption analyzer 150 may be configured to gather water temperature information relating to the water of the bathing unit 100. To that end, in this example of implementation, the optical absorption analyzer 150 comprises a temperature probe 180 for sensing the temperature of the water of the bathing unit 100. More specifically, in such embodiments, the temperature probe 180 makes a measurement of the temperature of the water and releases a signal conveying the recorded water temperature information to the processing unit 162. This may allow the processing unit 162 to use the water temperature information when deriving the concentration of the halogen H to compensate for effects that may be attributable to variations in water temperature rather than those that may be attributable to actual concentration of the halogen H.

Furthermore, optionally, in some embodiments, the optical absorption analyzer 150 may be configured to gather water acidity/basicity information related to the water of the bathing unit 100. To that end, the optical absorption analyzer 150 may comprise a pH (PH) probe 182 for sensing the water acidity/basicity level of the water of the bathing unit 100. More specifically, in such embodiments, the PH probe 182 makes a measurement of the acidity/basicity level of the water and releases a signal conveying the recorded water acidity/basicity information to the processing unit 162. This may allow the processing unit 162 to use the water acidity/basicity information when deriving the concentration of the halogen H to compensate for effects that may be attributable to variations in water acidity/basicity rather than those that may be attributable to actual concentration of the halogen H.

Once the processing unit 162 has derived an estimate of the concentration c of the halogen H in the sample of water 158, the optical absorption analyzer 150 releases a signal $S_c$ conveying the derived estimate of the concentration of the halogen H present in the sample of water 158. The signal $S_c$ released by the optical absorption analyzer 150 can be transmitted to one or more entities and used in various ways.

Figure 5A:
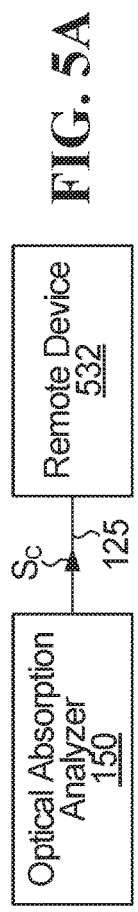
FIG. 5A is a functional block diagram showing transmission of a signal by the optical absorption analyzer of the device of FIG. 3 or the optical absorption analyzer of FIG. 4 to a remote computing device.
Figure 5B:
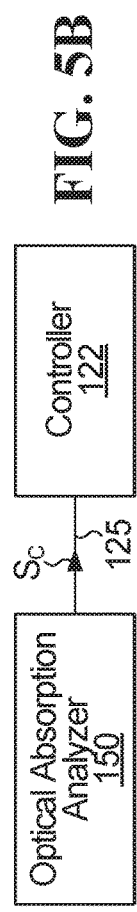
FIG. 5B is functional block diagram showing transmission of a signal by the optical absorption analyzer of the device of FIG. 3 or the optical absorption analyzer of FIG. 4 to a controller of the bathing unit system of FIG. 1.

In some embodiments, as shown in FIG. 5A, the signal $S_c$ released by the optical absorption analyzer 150 may be transmitted to a device 532 remote from the water analysis device 500 via a communication link 125 (e.g., a wired or wireless communication link). For instance, as shown in FIG. 3, the water analysis device 500 may optionally comprise an antenna 535 and suitable hardware/software modules for transmitting the signal $S_c$ to a remote device 532. The remote device 532 may include a display module and may be configured to display information conveying results obtained by the optical absorption analyzer 150. Notably, the remote device 532 may comprise a processing unit (not shown) and a display 534 for displaying information derived from the derived concentration of the specific halogen H. The remote device 532 may be embodied in any device suitable for a user to interact with. For instance, the remote device 532 may be a personal computing device or the bathing unit controller 122 of the bathing unit 100 (as shown in FIGS. 1 and 5B). The remote device 532 may alternatively be any other suitable type of device in other examples (e.g., desktop computer, a laptop, a tablet, a smart watch, a personal digital assistant (PDA), or any other suitable computing device etc.).

Figures 16, 17:
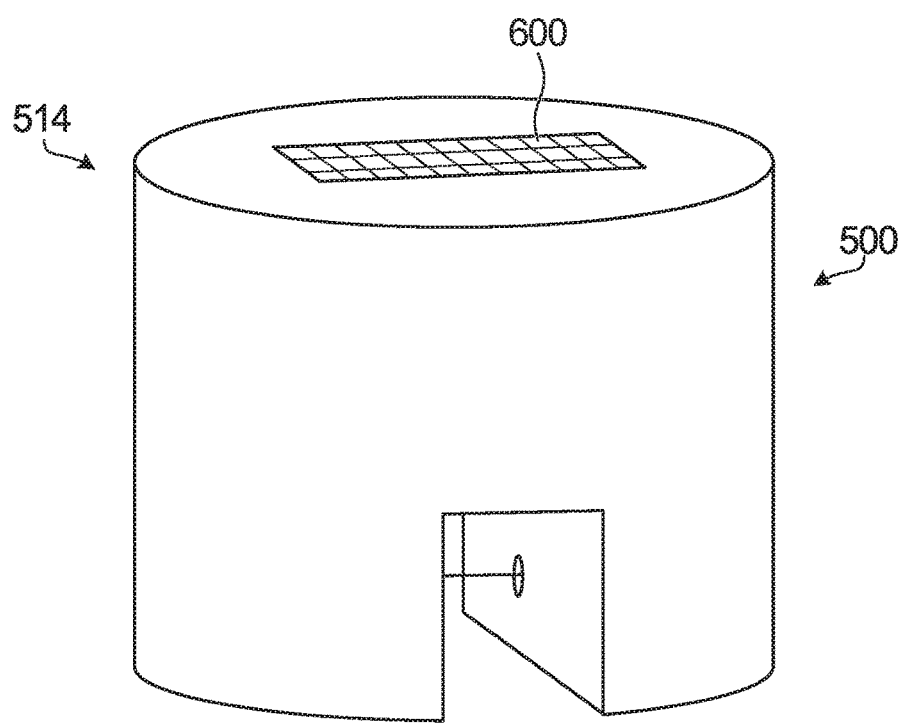
FIG. 16 shows an example of a lookup table that may be stored in a memory of a processing unit of the water analysis devices of the type shown in FIGS. 3, 7, 8 and 9 and/or in a memory of a bathing unit controller of the type depicted in FIG. 1.
FIG. 17 shows an example of an embodiment of a water analysis device in which a power source comprises a solar panel in accordance with a non-limiting example of implementation.

In some implementations, for example of the type shown in FIG. 5B, the signal $S_c$ released by the optical absorption analyzer 150 may be transmitted to the controller 122 of the bathing unit 100. In practical implementations, the communication link 125 between the optical absorption analyzer 150 and the controller 122 may be wire-line or wireless. In such a configuration, the controller 122 may be programmed to cause an action to be performed in dependence of the derived concentration of the halogen H. More specifically, in this example, the controller 122 may compare the derived concentration of the halogen H with a recommended range of concentration of the halogen H to determine if an action is to be taken. For instance, the controller 122 may comprise a memory (not shown) in which is stored recommended ranges of concentrations of respective halogens. This may be implemented as a lookup table 155 stored in the memory of the controller 122, an example of which is shown in FIG. 16. For example, the lookup table 155 may include recommended upper and lower limits of the concentration of the specific halogen H (e.g., $H_1$, $H_2$, $H_3$) such as a lower limit of 3 ppm and an upper limit of 5 ppm for bromine. The controller 122 may thus access the data stored in its memory and compare the derived concentration of the halogen H with the recommended range of concentration of the halogen H stored in its memory. Based on the comparison, the controller 122 determines if the derived concentration of the halogen H is greater, less than, or within the recommended range of concentration of the halogen H. The controller 122 may be programmed to implement an action at least partly dependent on its determination of where the derived concentration of the halogen H falls relative to the recommended range of concentration of the halogen H.

For instance, the controller 122 may derive control signals for conveying messages to the user of the bathing unit 100 in order to allow the user adjust the concentration of the halogen H in the water of the bathing unit 100. For example, if the controller 122 determines that the derived concentration of the halogen H is lower than the recommended range of concentration of the halogen H, the controller 122 may convey a message instructing the user to take steps to increase the halogen H in the water of the bathing unit 100. If the controller 122 determines that the derived concentration of the halogen H is greater than the recommended range of concentration of the halogen H, the controller 122 may convey a message instructing the user to limit (e.g., stop) adding halogen H to the water, or in some cases, to add water to the bathing unit 100.

In addition, or alternatively, the controller 122 may derive control signals for controlling operation of one or more devices of the bathing unit 100 in order to adjust the concentration of the halogen H in the water of the bathing unit 100. For example, if the controller 122 determines that the derived concentration of the halogen H is lower than the recommended range of concentration of the halogen H, the controller 122 may derive a control signal to cause an electrolytic cell 132 of the sanitizing system 130 to increase an input of the halogen H into the water of the bathing unit 100. If the controller 122 determines that the derived concentration of the halogen H is greater than the recommended range of concentration of the halogen H, the controller 122 may derive a control signal to cause the electrolytic cell 135 of the sanitizing system 130 to decrease an input of the halogen H into the water of the bathing unit 100 (e.g., to stop or reduce the generation of halogen H by a sanitizing device). This may allow the halogen H to evaporate from the water and thus reduce the concentration of the halogen H. Alternatively or additionally, the controller 122 may derive a control signal configured to control one or more valves (not shown) of the bathing unit 100 to add water into the circulation system 106 of the bathing unit 100 such as to reduce the concentration of the halogen H. For example, in such cases, the bathing unit 100 may also comprise a water outlet (e.g., a drain) through which water from the bathing unit 100 may be expelled and new water (i.e., water free of the halogen H) may be added via opening of the one or more valves, thus allowing a reduction of the concentration of the halogen H in the water of the bathing unit 100. The controller 122 may also store the derived concentration of the halogen H in its memory in a log of derived concentrations of the halogen H for future reference. In the event that the controller 122 determines that the derived concentration of the halogen H is within the recommended range of concentration of the halogen H, the controller 122 may store the derived concentration of the halogen H in its memory and not take any action to modify the concentration of the halogen H in the water of the bathing unit 100.

The transmittal of the signal $S_c$ to the controller 122 to cause an adjustment of an input of the halogen H into the water of the bathing unit 100 and/or to cause an adjustment of an input of water into the bathing unit 100 may thus create a closed loop feedback system where the concentration of the halogen H is continuously derived by the processing unit 162 of the optical absorption analyzer 150 and then adjusted in consequence with the derived concentration of the halogen H.

FIG. 6 shows a block diagram of a water flow path in which the water analysis device 500 is in-line with the circulation system 106 of the bathing unit 100 (as shown in FIG. 4). As shown, the water of the bathing unit 100 is monitored by the water analysis device 500 to monitor the concentration of the halogen H in the water, after which the water flows onwards in the circulation system 106 to be effected by the sanitizing system 130 on the basis of the concentration of the halogen H determined by the water analysis device 500 which, as discussed above, may increase or decrease the input of halogen H into the water based on the derived concentration of the halogen H. From there, the water flows into the receptacle 102 where the water is exposed to an environment of the receptacle 102 such that impurities may or may not be introduced into the water. The water then flows through the filter 124 where some impurities contained in the water may be removed, and then through the pump 112 where the water is pumped to circulate through the circulation system 106. The water then returns to the water analysis device 500 where the concentration of the halogen H in the water is monitored and the process restarts.

Figure 5C:
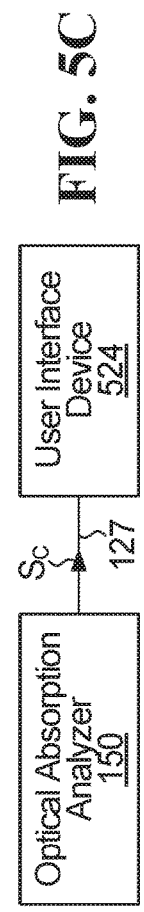
FIG. 5C is a functional block diagram showing transmission of a signal by the optical absorption analyzer of the device of FIG. 3 to a user interface part of the device of FIG. 3.

Alternatively or additionally, as shown in FIG. 5C, the signal $S_c$ released by the optical absorption analyzer 150 may be transmitted to the user interface device 524 of the device 150 with which the processing unit 162 is in electronic communication via a connection 127 (e.g., a wired or wireless connection). The user interface device 524 is configured to display information derived from the derived concentration of the halogen H. For example, the display 526 of the user interface device 524 displays a plurality of information elements 528, 530 derived from the derived concentration of the halogen H. For instance, in this example of implementation, a first information element 528 may consist of the derived concentration of the halogen H (e.g., "3.5 ppm") and a second information element 530 may consist of a status of the concentration of the halogen H relative to the recommended range of concentrations of the halogen H. The status of the concentration of the halogen H may be conveyed to the user in various ways. For example, in some cases, the second information element 530 may be a color (e.g., red, yellow, green, etc.), a symbol (e.g., an exclamation mark), a word (e.g., "LOW", "OK", "HIGH"), or any other suitable graphical element to convey to the user whether the derived concentration is below, within or above the recommend range of concentrations of the halogen. The information elements 528, 530 displayed by the display 526 are determined by the processing unit 162 at least in part on the basis of the derived concentration of the halogen H. For example, the processing unit 162 may store a lookup table similar to the lookup table 155 in its memory (not shown) in order to determine whether the derived concentration is outside of or within the recommended range of concentration of the halogen H and the processing unit determines the information elements 528, 530 to be displayed on that basis (e.g., red if the concentration of the halogen H is too low).

In some non-limiting implementations, the signal $S_c$ released by the processing unit 162 may be transmitted exclusively to the user interface device 524. That is, the signal $S_c$ released by the processing unit 162 may be transmitted exclusively locally to the water analysis device 500 such that the signal $S_c$ is not transmitted to the controller 122 of the bathing unit 100 or any other remote device 532.

Figure 14:
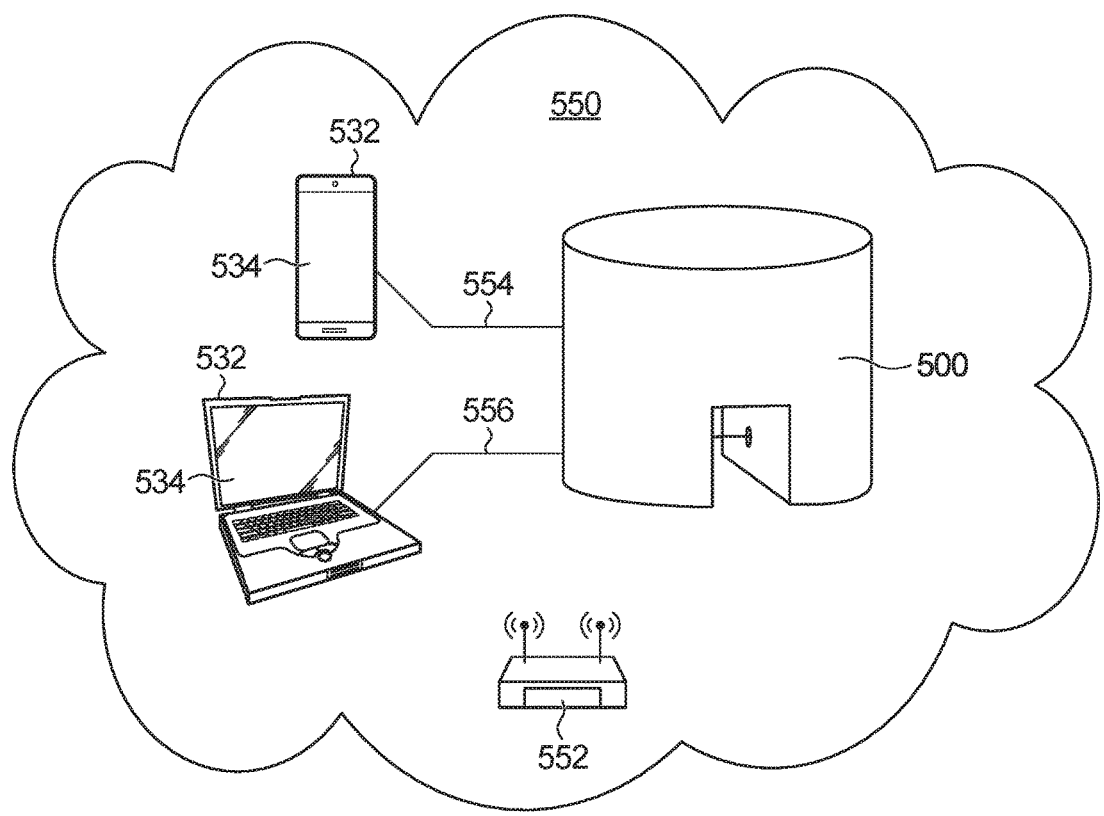
FIG. 14 shows an example of an embodiment in which the device of FIG. 3 is part of a communication network according to a non-limiting example.

Alternatively, as shown in FIG. 14, the water analysis device 500 may be part of a communication network 550 in which the water analysis device 500 can communicate with one or more other devices connected to the communication network 550. The communication network 550 may be a wired or wireless communication network. In the example depicted in FIG. 14, the communication network 550 is a (home) Wi-Fi network established by a router 552. More specifically, in this example of implementation, the water analysis device 500 communicates with a plurality of remote devices 532, including for example a smart phone and a laptop via respective wireless links 554, 556 established through the Wi-Fi network.

Alternatively still, the water analysis device 500 may communicate over a communication link (wireline or wireless) established directly one or more other devices, without the need for a WiFi network.

While embodiments of the optical absorption analyzer 150 have been described above, it will be appreciated that the configurations shown can be modified to account for additional factors and improve precision when deriving the concentration of the halogen H and/or to improve or otherwise facilitate deriving the concentration of the halogen H.

Some variants of the optical absorption analyzer 150 will now be described.

Reference Measurement of Light Emitted by the Light Source

In a first variant, the optical absorption analyzer 150 may be configured to make a measurement of the beam of light 154 emitted by the light source 152 before the light has travelled through the sample of water 158. This additional measurement serves as a "reference" measurement to allow the determination of the concentration of the halogen H to allow the processing unit 162 compensate for effects that may be attributable to variations in the ultraviolet light emitted by the light source 152 and/or received by the detector 156 rather than those that may be attributable to actual concentration of the halogen H. For example, such variations of the ultraviolet light emitted by the light source 152 and/or received by the detector 156 may be due to variations in the manufacturing of the light source 152, or the power source 165 and/or variations that occur over time as the light source 152 and/or the power source 165 age.

Figure 7:
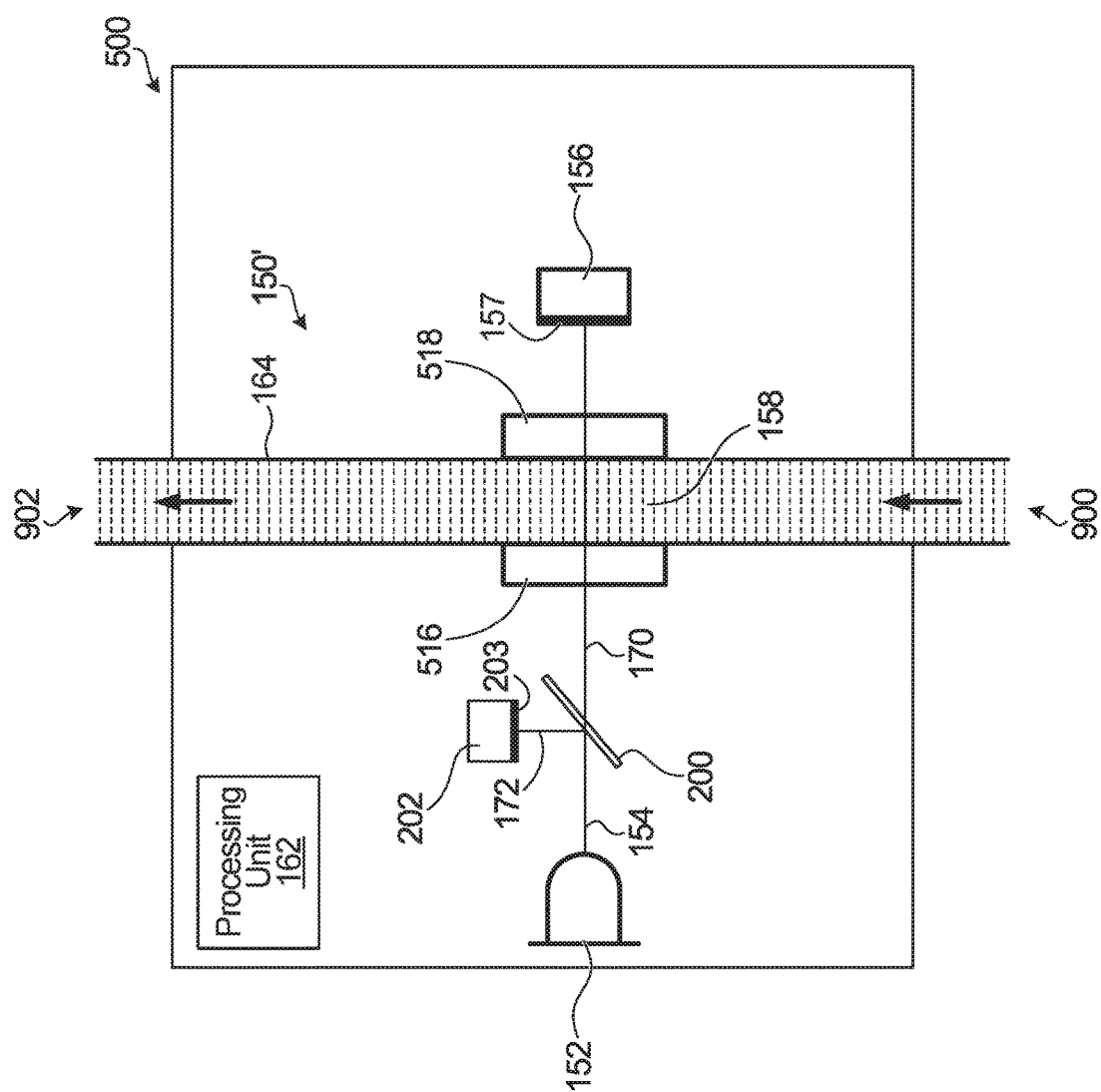
FIG. 7 is a diagram of a first variant of the in-line type of water analysis device shown in FIG. 4, wherein the water analysis device includes an optical absorption analyzer in accordance with a second specific implementation.

For instance, FIG. 7 shows a specific example of implementation in which an optical absorption analyzer 150' is configured substantially similarly to the optical absorption analyzer 150 depicted in FIGS. 3 and 4, with the exception that the optical absorption analyzer 150' comprises a second detector 202 in addition to the (first) detector 156. In this case, the second detector 202 is configured to make a reference measurement of the ultraviolet light emitted by the (first) light source 152 and may thus also be referred to as a "reference" detector 202.

More specifically, in use, the first detector 156 records a first measurement of ultraviolet light received from the light source 152 after the beam of light 154 has travelled through the sample of water 158 and the second detector 202 records a second measurement of ultraviolet light received from the light source 152 prior to the beam of light 154 having travelled through the sample of water 158. In other words, the second detector 202 receives the beam of light 154 in an "unmodified" state (i.e., without the beam of light 154 having travelled through the sample of water 158 and interacted with its chemical constituents). To that end, the second detector 202 is positioned on a same side of the sample of water 158 as the light source 152 such that the beam of light 154 does not traverse the sample of water 158 to reach the second detector 202. More particularly, in this embodiment, the second detector 202 is positioned such that its light-sensing surface 203 faces a direction transversal to the beam of light 154. In other words, the light-sensing surface 203 of the second detector 202 faces a direction transversal (e.g., generally perpendicular) to a direction faced by the light-sensing surface 157 of the first detector 156.

Moreover, in this embodiment, the optical absorption analyzer 150' comprises a beam splitter module 200 for directing a first portion 170 of the beam of light 154 toward the first detector 156 and a second portion 172 of the beam of light 154 toward the second detector 202. In other words, the beam splitter module 200 directs a first part of ultraviolet light generated by the light source 152 toward the first detector 156 and a second part of ultraviolet light generated by the light source 152 toward the second detector 202. In this example, the first and second portions 170, 172 of the beam of light 154 respectively directed to the first and second detectors 156, 202 are substantially equal to one another (i.e., the amount of light directed to the first and second detectors 156, 202 is similar). However, in other examples, the beam splitter module 200 may be configured to split the beam of light 154 such that a given one of the first and second portions 170, 172 of the beam of light 154 is greater than the other one of the first and second portions 170, 172 of the beam of light 154. For example, in some cases, the first portion 170 of the beam of light 154 that is directed to the first detector 156 may be greater than the second portion 172 of the beam of light 154 that is directed to the second detector 202. This may be helpful to ensure that an adequate amount of light reaches the first detector 156 which may be further from the light source 152 than the second detector 202.

In some specific practical implementations, the beam splitter module 200 may comprise a semi-transparent body to allow the first portion 170 of the beam of light 154 to be transmitted through to the first detector 156 and the second portion 172 of the beam of light 154 to be reflected to the second detector 202.

Figure 8:
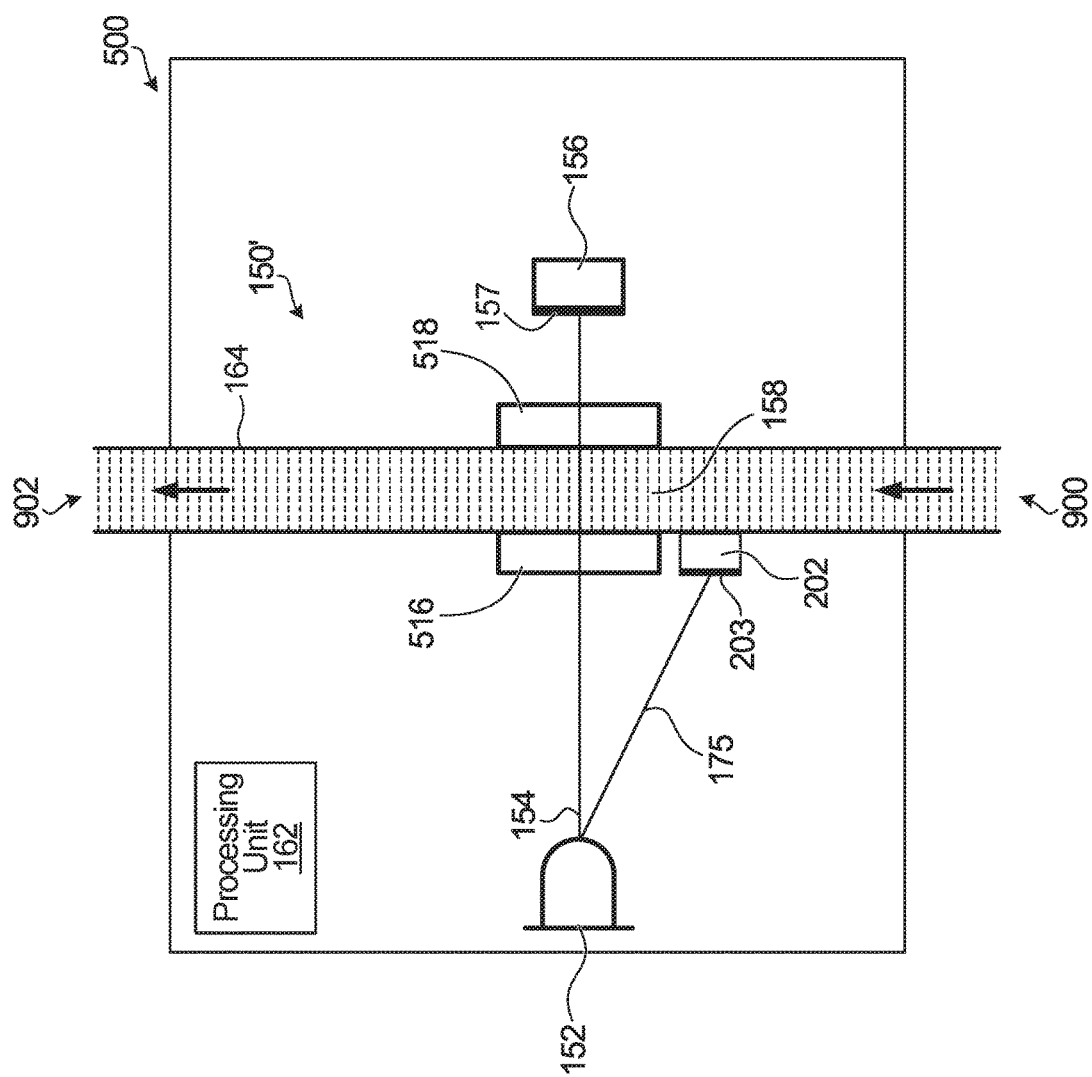
FIG. 8 is a diagram of a second variant of the in-line type of water analysis device shown in FIG. 4, wherein the water analysis device includes an optical absorption analyzer in accordance with a third specific implementation.

In other embodiments, as shown in FIG. 8, rather than the beam of light 154 being directed to the second detector 202 by a beam splitter module 200, the second detector 202 may be configured to receive light directly from the light source 152. For instance, the second detector 202 may be positioned to receive a portion 175 of the light emitted by the light source 152 that is outside of a cone of light collimated and directed to the sample of water 158. To that end, in such embodiments, the second detector 202 is positioned such that its light-sensing surface 203 faces the light source 152. For example, the light-sensing surface 203 of the second detector 202 may face the same direction as the light-sensing surface 157 of the first detector 156.

With the configurations of the optical absorption analyzer 150' described above with reference to FIGS. 7 and 8, the processing unit 162 can derive an estimate of the concentration of the halogen H at least in part by processing results of the first and second measurements effected by the first and second detectors 156, 202 respectively. More specifically, based on the reference measurement of the light source 162 effected at the second detector 202, the processing unit 162 can calculate calibration coefficients that account for the variations in the power of the light source 152 and which may thus improve accuracy of the derived concentration of the halogen H.

More specifically, the radiant flux $\varphi_e^i$ incident on the sample of water 158 can be measured using the signal $S_R^A$ recorded by the second detector 202 while the transmitted radiant flux $\varphi_e^t$ (i.e., the radiant flux received at the first detector 156) can be measured using the signal $S_A^A$ recorded by the first detector 156. The first and second detector chains have their own specific response functions $R_R$ and $R_A$, such that the recorded signals $S_R^A$, $S_A^A$ are given by Equations 2 and 3 reproduced below:

$$S_R^A = R_R \varphi_e^i \quad \text{(Equation 2)}$$

$$S_A^A = R_A \varphi_e^t \quad \text{(Equation 3)}$$

Replacing Equations 2 and 3 into Equation 1 results in Equation 4 reproduced below:

$$\log\left(\frac{\frac{S_R^A}{R_R}}{\frac{S_A^A}{R_A}}\right) = \varepsilon c l \quad \text{(Equation 4)}$$

Similar to what was described above, the optical absorption analyzer 150' derives an estimate of the concentration c of the halogen H. To do so, Equation 4 can be transformed into Equations 5 and 6, shown below, where α and β are calibration coefficients:

$$c = \frac{1}{\varepsilon l}\log\left(\frac{\frac{S_R^A}{R_R}}{\frac{S_A^A}{R_A}}\right) \quad \text{(Equation 5)}$$

$$c = \alpha\log\left(\beta\frac{S_R^A}{S_A^A}\right) \quad \text{(Equation 6)}$$

The calibration coefficient β is defined as a ratio of the first detector chain response $R_A$ over the reference detector chain response $R_R$ as given by Equation 7 shown below:

$$\beta = \frac{R_A}{R_R} \quad \text{(Equation 7)}$$

The calibration coefficient β can be measured by using a sample of water containing no target halogen (i.e., the concentration c of the halogen H=0) in which case Equation 6 transforms into Equation 8 shown below:

$$0 = \log\left(\beta\frac{S_R^A}{S_A^A}\right) \quad \text{(Equation 8)}$$

Equation 8 can be solved to obtain Equations 9 and 10 shown below:

$$1 = \beta\frac{S_R^A}{S_A^A} \quad \text{(Equation 9)}$$

$$\beta = \frac{S_A^A}{S_R^A} \quad \text{(Equation 10)}$$

Using Equation 10, the calibration coefficient β can be calculated as a ratio of the detector signal $S_A^A$ over the detector signal $S_R^A$, when the concentration c of the halogen H is null (in other words no halogen in the water). Meanwhile, the calibration coefficient α in Equation 6 can be calculated by using an etalon sample (i.e., a sample having standard known properties) with a known concentration c of the halogen H (c=$c_0$, as measured by other methods, such as for example using a Bromine titration test kit). As such, Equation 6 can be transformed into Equation 11 as shown below:

$$\alpha = \frac{c_0}{\log\left(\beta\frac{S_R^A}{S_A^A}\right)} \quad \text{(Equation 11)}$$

In other words, Equation 11 can be used to calculate the calibration coefficient α using the calibration coefficient β, and the detector signals $S_R^A$, $S_A^A$ measured with the etalon sample.

Using Multiple Light Sources of Different Wavelengths

In another variant, the optical absorption analyzer may be configured to make a measurement of light emitted at a wavelength that the halogen H does not substantially absorb in addition to the measurement made to gauge the light emitted by the light source 152 whose wavelength the halogen H substantially absorbs. This may allow the determination of the concentration of the halogen H to compensate for effects that may be attributable to impurities in an optical path between the light source 152 and the first detector 156 rather than those that may be attributable to actual concentration of the halogen H in the sample of water 158. For example, such impurities may be due to sand particles in the sample of water 158 and/or particles having adhered to the windows 516, 518 between the light source 152 and the first detector 156.

Figure 9:
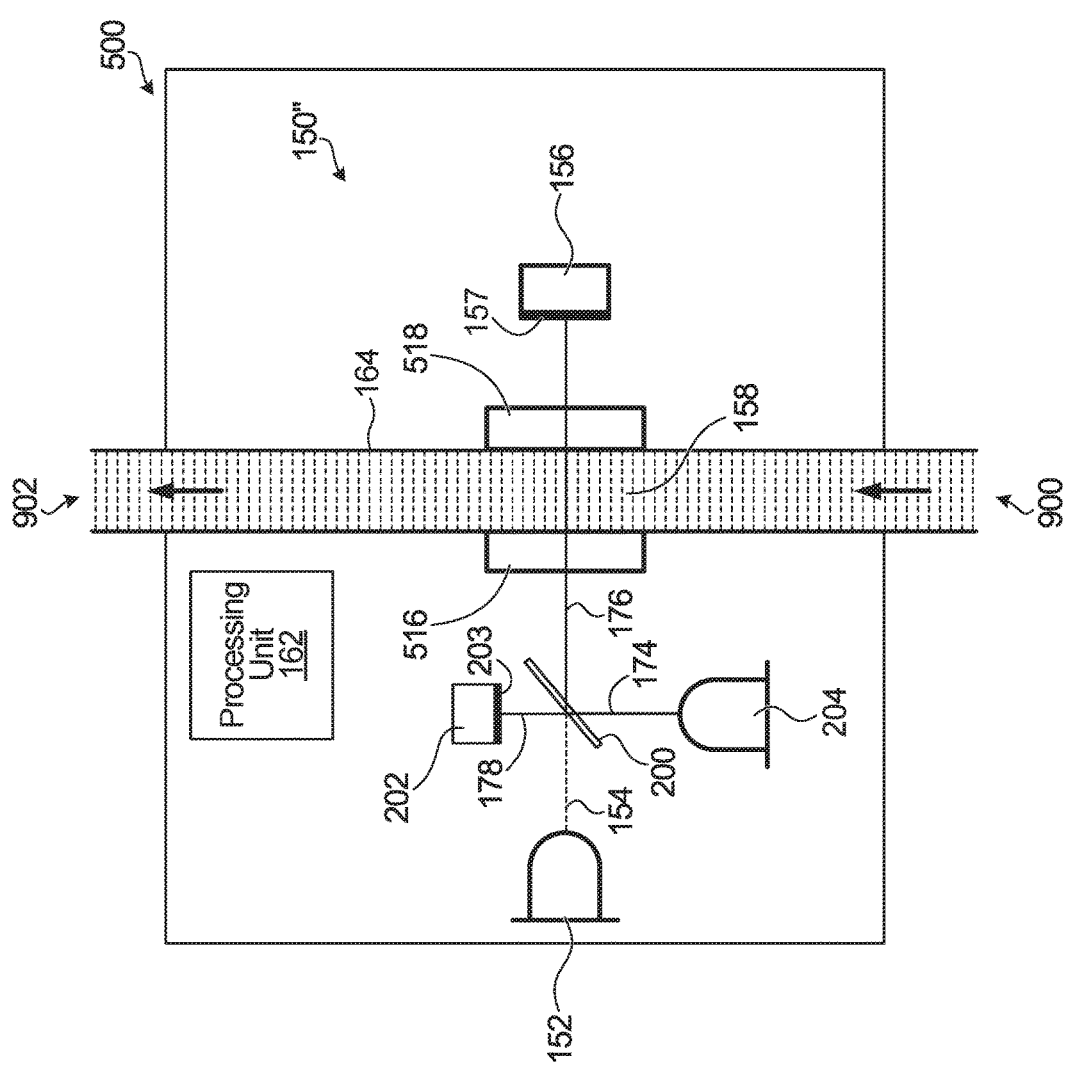
FIG. 9 is a diagram of a third variant of the in-line type of water analysis device shown in FIG. 4, wherein the water analysis device includes an optical absorption analyzer in accordance with a fourth specific implementation.

For instance, FIG. 9 shows a specific example of implementation in which an optical absorption analyzer 150" is configured substantially similarly to the optical absorption analyzer 150' depicted in FIG. 7, with the exception that the optical absorption analyzer 150" comprises a second light source 204 in addition to the (first) light source 152. The second light source 204 emits a beam of light 174 that is received by the first detector 156 for measurement of the light emitted by the second light source 204. The beam of light 174 emitted by the second light source 204 has a wavelength that is different from the wavelength of the beam of light 154 emitted by the first light source 152. Specifically, the wavelength of the beam of light 174 emitted by the second light source 204 is such that the beam of light 174 is substantially not absorbed by the halogen H. That is, the wavelength of the beam of light 174 is generally unaffected by the concentration of the halogen H in the sample of water 158. As the second light source 204 is used as a reference, the second light source may be referred to as a "reference" light source. In this embodiment, the wavelength of the beam of light 174 may emit light in the visible or near-infrared range of the spectrum (e.g., about 400 nm to 1100 nm) rather than in the ultraviolet range. For instance, in some cases, the wavelength of the beam of light 174 may be between about 450 nm and 600 nm, in some cases between about 475 nm and 550 nm, and in some cases about 500 nm.

In this example of implementation, the first detector 156 records a first measurement of ultraviolet light received from the first light source 152 and the second detector 202 records a second measurement of ultraviolet light received from the first light source 152 prior to the beam of light 154 having travelled through the sample of water 158. The first detector 156 then records a first measurement of light received from the second light source 204 and the second detector 202 records a second measurement of light received from the second light source 204 prior to the beam of light 174 having travelled through the sample of water 158 (i.e., without the beam of light 174 having traversed the sample of water 158 and interacted with its chemical constituents). As such, in this example, the same first detector 156 is used for making the first measurements of transmission of light from the first and second light sources 152, 204, and the same second detector 202 is used for making the second measurements of transmission of light from the first and second light sources 152, 204 prior to the light of the respective light sources travelling through the sample of water 158.

In this example of implementation, the first and second light sources 152, 204 are sequentially turned "ON" and "OFF" to allow the detectors 202 and 156 to make their respective measurements. More specifically, the first light source 152 is turned "ON" (i.e., to emit light) for a period of time and then turned "OFF" (i.e., to cease emitting light)

to allow the second light source 204 to be turned "ON" for a period of time and then turned "OFF". With this cycled approach the optical absorption analyzer 150" can be referred to as a sequential two-wavelength analyzer. In order to derive an estimate of the concentration of the halogen, the processing unit in FIG. 9 may make use of Equations 1 to 11, which also apply to the second light source 204 albeit with a new molar attenuation coefficient ε and new calibration coefficients α and β, all three variables being selected for the wavelength of the second light source 204.

The second light source 204 is positioned on the same side of the sample of water 158 as the light source 152 such that the beam of light 174 has to traverse the sample of water 158 to reach the second detector 202. More particularly, in this embodiment, the second light source 204 is positioned such to face a direction transversal (e.g., generally perpendicular) to a direction faced by the first light source 152.

Thus, in order to direct the beam of light 174 emitted by the second light source 204 to the first detector 156, the beam splitter module 200, in addition to being configured to split the beam of light 154 emitted by the first light source 152, is configured to split the beam of light 174 emitted by the second light source 204. Notably, the beam splitter module 200 directs a first portion 176 of the beam of light 174 towards the first detector 156 and a second portion 178 of the beam of light 174 towards the second detector 202. In this example, the first and second portions 176, 178 of the beam of light 174 respectively directed to the first and second detectors 156, 202 are substantially equal to one another (i.e., the amount of light directed to the first and second detectors 156, 202 is similar). However, in other examples, the beam splitter module 200 may be configured to split the beam of light 174 such that a given one of the first and second portions 176, 178 of the beam of light 154 is greater than the other one of the first and second portions 176, 178 of the beam of light 154. For example, in some cases, the first portion 176 of the beam of light 174 that is directed to the first detector 156 may be greater than the second portion 178 of the beam of light 154 that is directed to the second detector 202.

With the configuration of the optical absorption analyzer 150" described above, the processing unit 162 can derive the concentration of the halogen H at least in part by processing results of the first and second measurements of transmission of light from the first light source 152 and the first and second measurements of transmission of light from the second light source 204. More specifically, based on the measurements of the light received from the second light source 204, the processing unit 162 can calculate a calibration coefficient that accounts for the impurities and whose inclusion in calculating the concentration of the halogen H may thus improve an accuracy of the derived concentration of the halogen H. This calibration coefficient may thus be referred to as an "interference coefficient" in some cases.

Notably, according to the principles of optical absorption, when two chemical species (labeled 1 and 2) are present in the sample of water 158, the Beer-Lambert equation becomes Equation 12 for the first light source 152 and Equation 13 for the second light source 204, as shown below:

$$\log\left(\frac{\frac{S_R^A}{R_R}}{\frac{S_A^A}{R_A}}\right) = \varepsilon_1^A c_1 l_1^A + \varepsilon_2^A c_2 l_2^A \quad \text{(Equation 12)}$$

$$\log\left(\frac{\frac{S_R^R}{R_R}}{\frac{S_A^R}{R_A}}\right) = \varepsilon_1^R c_1 l_1^R + \varepsilon_2^R c_2 l_2^R \quad \text{(Equation 13)}$$

Equation 14, reproduced below, is obtained by subtracting Equation 13 from Equation 12:

$$\log\left(\frac{\frac{S_R^A}{R_R}}{\frac{S_A^A}{R_A}}\right) - \log\left(\frac{\frac{S_R^R}{R_R}}{\frac{S_A^R}{R_A}}\right) = \varepsilon_1^A c_1 l_1 + \varepsilon_2^A c_2 l_2 - (\varepsilon_1^R c_1 l_1 + \varepsilon_2^R c_2 l_2) \quad \text{(Equation 14)}$$

If the first light source 152 and the second light source 204 are collinear, the optical pathlengths for their beams can be considered to be equal, as expressed in Equations 15 and 16 below:

$$l_1^A = l_1^R = l_1 \quad \text{(Equation 15)}$$

$$l_2^A = l_2^R = l_2 \quad \text{(Equation 16)}$$

The optical pathlength $l_1$ (for the first light source 152) is kept distinct from the optical pathlength $l_2$ (for the second light source 204) to cover cases for example where the chemical species 2 is deposited on the windows 516, 518 as a thin layer and chemical species 1 is present throughout the volume of the sample of water 158. By combining Equations 14, 15 and 16, Equations 17 and 18 are obtained as shown below:

$$\log\left(\frac{\frac{S_R^A}{R_R}\frac{S_A^R}{R_A}}{\frac{S_A^A}{R_A}\frac{S_R^R}{R_R}}\right) = c_1 l_1 (\varepsilon_1^A - \varepsilon_1^R) + c_2 l_2 (\varepsilon_2^A - \varepsilon_2^R) \quad \text{(Equation 17)}$$

$$\log\left(\frac{S_R^A S_A^R}{S_A^A S_R^R}\right) = c_1 l_1 \xi_1 + c_2 l_2 \xi_2 \quad \text{(Equation 18)}$$

In Equations 17 and 18, $\xi_1$ and $\xi_2$ are the effective molar attenuation coefficients as defined in Equations 19 and 20 shown below:

$$\xi_1 = \varepsilon_1^A - \varepsilon_1^R \quad \text{(Equation 19)}$$

$$\xi_2 = \varepsilon_2^A - \varepsilon_2^R \quad \text{(Equation 20)}$$

The second light source 204 can be chosen to emit wavelengths so that the molar attenuation coefficient of the second interfering chemical species is substantially the same as for the first light source 152.

A granular opaque inhomogeneous contaminant such as dirt can cause this type of progressive decrease of transmission affecting wavelengths of light emitted by the first and second light sources 152, 204 in a similar manner. One can also find a wavelength for the second light source 204 so that a film of matter reduces the light intensity in a manner similar to the wavelength of the light beam 154 emitted by the first light source 152. When this happens, $\xi_2 = 0$, as can be seen in Equation 21 below:

$$\xi_2 = \varepsilon_2^A - \varepsilon_2^R = 0 \quad \text{(Equation 21)}$$

To illustrate the above, let us say that we have an interfering species in the optical path between the first light source 153 and the detector 156. If this species is interfering, it means that it absorbs at the wavelength at which the first light source 152 is emitting light, the same wavelength used to measure the concentration of the specific halogen H. If only one wavelength is used, the presence of this interfering species in the optical path will reduce the intensity of the wavelength received at the detector 156 and the optical absorption analyzer will "think" that a greater concentration of halogen H is present in the water.

By choosing the wavelength of the second light source 204 so the interfering species absorbs the same amount at the wavelength of the second light source 204 and at wavelength of the first light source 152, a simplification occurs as can be seen by equations 19 and 20 above and the information provided by the second light source 204 allows us to compensate for this interfering absorption in order to derive an estimate of the concentration of halogen H where the effects of the interfering species have been compensated.

One example is dirt accumulating on the window. Assume that each grain of dirt is 100% absorbing at all wavelengths (opaque). The transmittance of the window will be given only by the percentage of surface covered by this opaque material. Another example would be a material that attenuates all wavelengths by the same ratio, a neutral absorber. In both of these examples Equation 21 holds.

A specific non-limiting way to achieve the condition in equation 21 is to choose the wavelength of the second light source 204 to be as close as possible to the wavelength of the first light source 152, while being away from the maximum absorption wavelength of the halogen H.

Equation 22, reproduced below, can be obtained by replacing Equation 21 in Equation 18:

$$c_1 = \gamma_1 \log\left(\frac{S_R^A S_A^R}{S_A^A S_R^R}\right) \quad \text{(Equation 22)}$$

Equation 22 contains a calibration coefficient $\gamma_1$ that can be calculated using an etalon sample with a known concentration of the halogen H ($c_1 = c_0$), as measured by another method. In this case, the calibration coefficient $\gamma_1$ (which we can also refer to as the interference coefficient) can be obtained by Equation 23 shown below:

$$\gamma_1 = \frac{c_1}{\log\left(\frac{S_R^A S_A^R}{S_A^A S_R^R}\right)} \quad \text{(Equation 23)}$$

The "ideal" optical absorption analyzer 150" would be configured such that the halogen H absorbs strongly at the wavelengths of the light emitted by the first light source 152 and not at all, or in practice significantly less, at the wavelengths of the light emitted by the second light source 204. In this "ideal" optical absorption analyzer 150", the second light source 204 is chosen so there is negligible absorption by the halogen H at the wavelength of the light emitted by the second light source 204. If this is not possible, the optical absorption analyzer 150" will still produce a usable result as long as the absorption of light by the halogen H is sufficiently different at the wavelength of the light emitted by the first light source 152 and at the wavelength of the light emitted by the second light source 204.

Optionally, in some embodiments, the water analysis device 500 may use the interference-related information (e.g., the interference coefficient $\gamma_1$) to inform the user of a cleanliness status of the water and the windows 516, 518 of the housing 502.

More specifically, in some embodiments, the processing unit 162 of the water analysis device 500 may be configured to transmit to the user interface device 524 of the water analysis device 500, and/or the remote device 532 to which the water analysis device 500 is connected, the interference-related information gathered from monitoring the sample of water 158. For instance, in addition to the derived concentration of the halogen H, the signal $S_C$ transmitted by the processing unit 162 to the user interface device 524 and/or the remote device 532 may include the interference-related information. In turn, the user interface device 524 and/or the remote device 532 may display information derived from the interference-related information received in the signal $S_C$. For instance, in a specific example of implementation, as shown in FIG. 13, the display 526 of the user interface device 524 may display a third information element 531 derived from the interference-related information. For example, the third information element 531 may consist of a cleanliness status of the water and/or of the windows 516, 518 of the housing 502 which may be expressed graphically or numerically in any suitable way. In this example, the cleanliness status is expressed as a rating on a given scale (e.g., 1/10, 2/10, 3/10, etc.) to inform the user of the cleanliness of the water of the bathing unit 100 and/or of the windows 516, 518 of the housing 502. This may be advantageous for the user to take action, if necessary, based on the cleanliness status displayed by the user interface device 524 and/or the remote device 532. For example, the user may be compelled to clean the windows 516, 518 of the housing 502 and/or verify the functionality of the filter 124 of the bathing unit 100.

Using Light Sources of Different Wavelengths and Operating them at Different Frequencies In some variants, the first and second lights sources 152, 204 of the optical absorption analyzer 150" depicted in FIG. 9 may be continuously left "ON" and may be operated according to an intermittent (e.g., periodic) light pattern (e.g., with a variable modulation), such as for example, but without being limited to, a sinusoidal light pattern or a square wave light pattern. Advantageously, keeping the first and second light sources 152, 204 "ON" and operating them according to an intermittent light pattern may present a number of advantages including reducing transition effects caused by activating/deactivating the light sources 152, 204.

In order to achieve this, the first and second light sources 152, 204 may be operated at different frequencies. For instance, the first light source 152 emits light at a first frequency $F_1$ and the second light source 204 emits light at a second frequency $F_2$ different from the first frequency $F_1$. Preferably, the first and second frequencies $F_1$ and $F_2$ are selected so that they are not harmonics of one another. In this embodiment, the optical absorption analyzer 150" may be configured to derive the concentration of the specific halogen H at least in part based on a frequency distribution associated with the results of the first and the second measurements of the transmission of light from the first light source 152 and the results of the first and the second measurements of the transmission of light from the second light source 204. Advantageously, by selecting certain first and second frequencies, effects of some external sources of interference may be reduced on the measurements of the transmission of light from the first and second light sources 152, 204. External sources of interference may include, for example but without being limited to, changes in ambient light (for example due to the time of day, the amount of sun, the type of light, clouds, etc.) as well as the presence of electrical/electronic EM fields (typically caused by the electrical grid—60 Hz, 120 Hz and harmonics (240 Hz, 480 Hz, etc.)).

In some specific practical applications, the first and second frequencies $F_1$, $F_2$ may be chosen so that they are not harmonics of one another and so that they are not harmonic of signals that are considered "noise" (e.g. electrical/electronic signals). In a specific non-limiting example of implementation, the first frequency $F_1$ is greater than the second frequency $F_2$. For instance, the first frequency $F_1$ may be between 420 and 580 Hz, such as for example about 450 Hz. Furthermore, the second frequency $F_2$ may be above 350 Hz, such as for example between 350 Hz and 200 kHz, in some cases between 400 Hz and 1 kHz, in some cases between 500 Hz and 800 Hz, in some cases between 540 Hz and 600 Hz, such as for example about 570 Hz.

In this embodiment, the signals produced by the light received at the first and second detectors 156, 202 are composed of a superposition of the signals produced by light emitted by each of the first and second light sources 152, 204. The amplitude of the signals recorded at the first and second detectors 156, 202 can be derived by applying a Fourier transform demodulation to obtain a frequency domain representation of the signals recorded at the first and second detectors 156, 202. The signals produced by the light of the first and second light sources 152, 204 have amplitudes $A_1$, $A_2$ (which may correspond to the signals $S_R^A$, $S_R^R$ in equation 22 above). FIG. 12A depicts a frequency domain representation of signals received at the first detector 156, and shows that the signal recorded at the first detector 156 has peak amplitudes $A_1'$, $A_2'$ which are smaller than the original amplitudes $A_1$, $A_2$ (shown in FIG. 12B) measured at the second detector 202. This variation in amplitude may be attributed to an absorption of light by the halogen H and by impurities contained in the sample of water 158. The maximum amplitudes $A_1'$, $A_2'$ (which may correspond to the signals $S_A^A$, $S_A^R$ in equation 22 above) forming the peaks of the signal, or the area of the peaks may be used. In this example, the greater amplitude $A_2'$ corresponds to the light received from the second light source 204 at the first detector 156 at the second frequency $F_2$ and the smaller amplitude $A_1'$ corresponds to the light received from the first light source 152 at the first detector 156 at the first frequency $F_1$.

FIG. 12B depicts the frequency domain representation of the signals received at the second detector 202, and shows that the signal recorded at the second detector 202 has peak amplitudes $A_1$, $A_2$ which are approximately equal to one another in this example. Using $A_1$, $A_2$ $A_1'$, $A_2'$ in equation 22, an estimate of the concentration of halogen H in the sample of water 158 can be derived.

In specific implementations, the first and second signals are modulated in order to shift these signals away from interfering signals. Choosing two distinct frequencies for the two sources allows us to operate them simultaneously, removing the need to various timed sequences (source 152 "ON", source 204 "OFF", etc. . . . ). Demodulation (Fourier transform) allows separating the signals from interfering influences occurring at other frequencies. In specific implementation, the first and second frequencies of modulation of the light sources may be chosen at frequencies where minimal amounts of interference exist.

alternatively, the first and second frequencies of the light sources may be chosen to be sufficiently high so that a high pass filter may in some cases be used to filter out effects of changes in ambient light, which would typically be at relatively low frequencies (e.g., such as the passage of a cloud). In addition, a suitable filter, such as a band-pass filter, may be used to filter out effects of the electrical/electronic signals (e.g., by discriminating against selected frequencies such as 60 Hz, 120 Hz and harmonics) without hindering the first and second frequencies $F_1$, $F_2$ of the first and second light sources 152, 204. In such cases, the first and second frequencies $F_1$, $F_2$ of the light sources 152, 204 may be chosen not to correspond to a harmonic of the electrical/electronic signals.

Processing Unit 162

Figure 10:
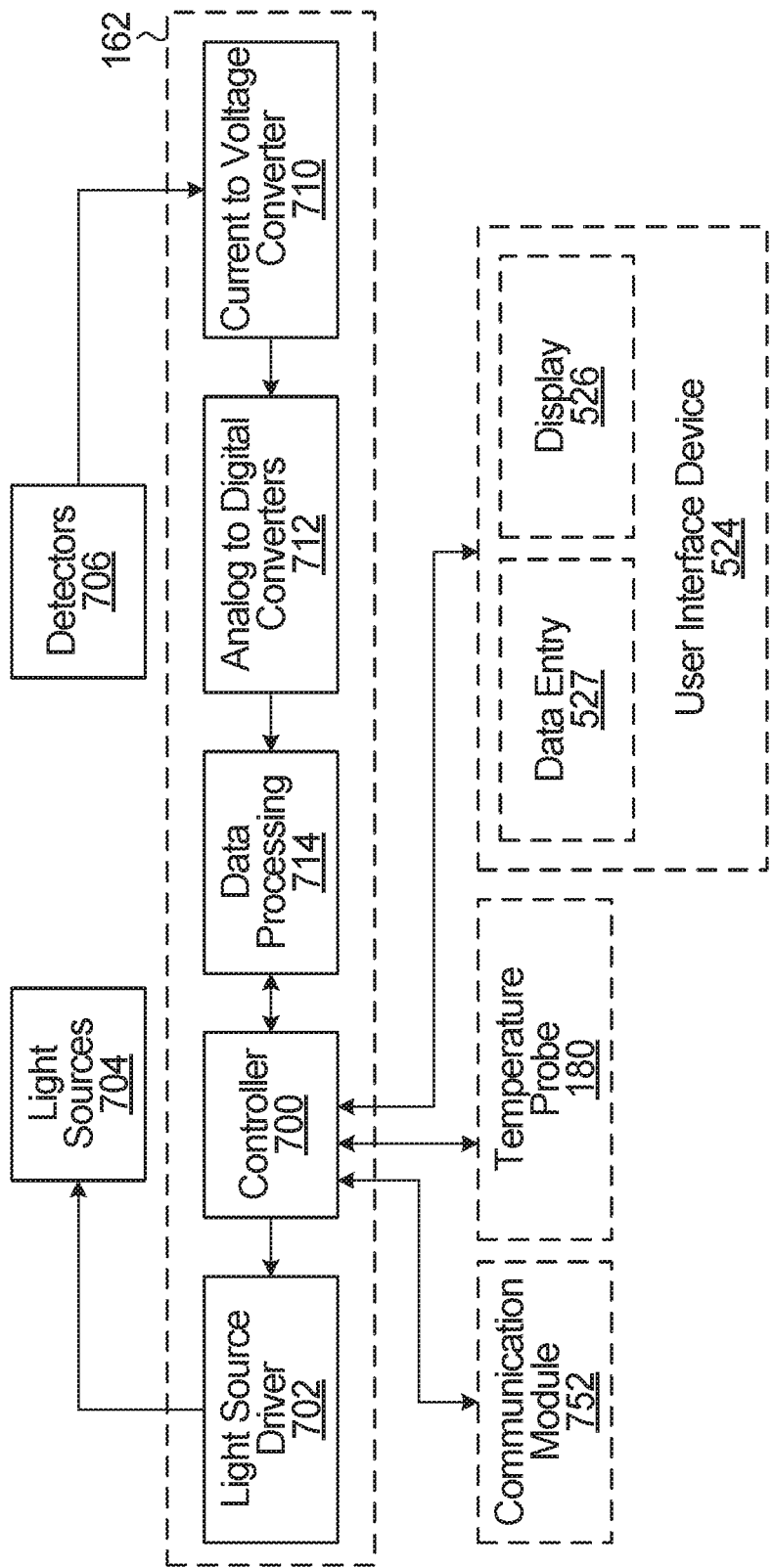
FIG. 10 is a block diagram, showing some functional modules of a processing unit that may be used in connection with the water analysis device shown in FIGS. 3, 4, 7, 8 and 9 in accordance with non-limiting examples of implementation of the invention.
Figure 11:
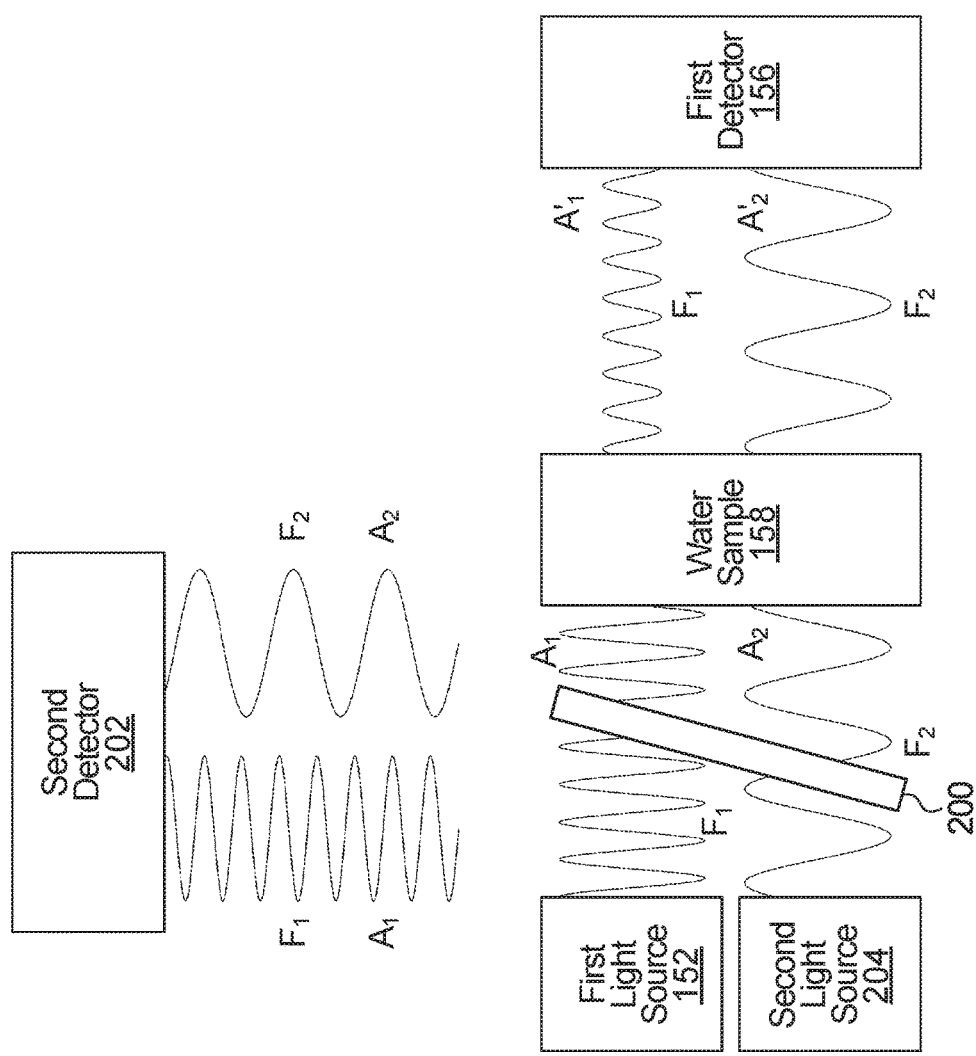
FIG. 11 shows a functional diagram of components of a water analysis device using alternating light sources in accordance with a variant of implementation of the water analysis device shown in FIG. 9.

FIG. 10 depicts a functional block diagram of processing unit 162 in accordance with a specific embodiment. In this embodiment, the processing unit 162 of the optical absorption analyzer 150, 150' and 150" comprises a controller 700 configured to receive inputs from and issue outputs to other modules of the processing unit 162 and entities outside of the processing unit 162. For example, the controller 700 is in communication with a light source driver 702 of the processing unit 162 that is configured to send a signal to one or more light sources 704 (e.g., first and second light sources 152, 204) of the optical absorption analyzer 150, 150', 150" to actuate/deactivate the one or more light sources 704. The processing unit 162 also comprises a current to voltage converter 710 in communication with one or more detectors 706 (e.g., first and second detectors 156, 202) and configured to produce a voltage proportional to a current received from the signal transmitted to the processing unit 162 by the detectors 706. The current to voltage converter 710 is in communication with an analog to digital converter 712 which converts the analog signal produced by the current to voltage converter 710 into a digital signal. The digital signal produced by the analog to digital converter 712 is then transmitted to a data processing module 714 of the processing unit 162, where the data contained in the digital signal transmitted to the data processing module 714 is processed. For example, the data processing module 714 may be configured to derive an estimate of the concentration of the halogen H in the manner described above.

The controller 700 comprises a memory (not shown) for storing data therein. More specifically, the memory 165 may store data related to operation of the water analysis device 500. For example, this may include operational parameters of the optical absorption analyzer 150 and/or reference data related to one or more halogens which can be monitored by the water analysis device 500. For example, the lookup table previously discussed, similar to the lookup table 155 depicted in FIG. 16, may be stored in the memory of the controller 700. Other data related to operation of the water analysis device 500 may also be stored in the memory of the controller 700. For example, data related to the wavelength associated with the different light sources, frequencies at which the light sources can be operated and other such data is stored in the memory of the controller 700.

The controller 700 also receives inputs from and issue outputs to entities outside of the processing unit 162. For instance, the controller 700 may be in communication with a temperature probe 180 to receive the signal conveying the temperature of the water. Moreover, the controller 700 may be in communication with the user interface device 524, including the display 526 and the data entry module 527. This may be useful to allow a user to provide information related to operation of the water analysis device 500 into the processing unit 162. For example, this may include making a selection of the halogen H which is intended to be monitored by the water analysis device 500. As another example, this may allow connecting the device 500 to the communication network 550 (e.g., entering a password to a Wi-Fi network).

In embodiments where the water analysis device 500 is part of the communication network 550, as depicted in FIG. 14, the controller 700 may interface with the communication network 550 via a communication module 752. The communication module 752 may be for example a receiver, transmitter or transceiver that allows the processing unit 162 to communicate with the communication network 550.

The embodiments described above are intended to be exemplary only.

It will be apparent to the person skilled in the art in light of the specification that many variations are possible. For example, while embodiments of devices described in the present application including a processor programmed for deriving the concentration of a specific halogen by processing various measurements of light transmission obtained by photo-detectors of the apparatus, it is to be appreciated that such computations need not occur in the device 500 itself but may in some implementations be implemented by processors located remotely from the device 500, including processors that may be located at the bathing unit controller 122 or in the cloud. In such cases measurements of light transmission, once obtained by the photo-detectors, would be transmitted to the remote location including one or more processor programmed for implementing some of the processing functionality, including some of the computations, described in the present application.

It will also be understood by those of skill in the art that throughout the present specification, the term "a" used before a term encompasses embodiments containing one or more to what the term refers. It will also be understood by those of skill in the art that throughout the present specification, the term "comprising", which is synonymous with "including," "containing," or "characterized by," is inclusive or open-ended and does not exclude additional, un-recited elements or method steps.

Unless otherwise defined, all technical and scientific terms used herein have the same meaning as commonly understood by one of ordinary skill in the art to which this invention pertains. In the case of conflict, the present document, including definitions will control.

As used in the present disclosure, the terms "around", "about" or "approximately" shall generally mean within the error margin generally accepted in the art. Hence, numerical quantities given herein generally include such error margin such that the terms "around", "about" or "approximately" can be inferred if not expressly stated.

Although various embodiments of the invention have been described and illustrated, it will be apparent to those skilled in the art in light of the present description that numerous modifications and variations can be made. The scope of the invention is defined more particularly in the appended claims.

The invention claimed is:

1. A device for monitoring a concentration of a specific halogen in a bathing unit, said device comprising:
   a. a housing configured for floating on top of a body of water held in a receptacle of the bathing unit, said housing having a lower portion configured for being at least partially submerged in water during use and an upper portion configured for extending at least partially above the water, said lower portion including walls extending into the water and defining spaced apart opposing windows made at least in part of a material permeable to ultraviolet light;
   b. an optical absorption analyzer positioned within said housing, said optical absorption analyzer being configured for making measurements of transmission of ultraviolet light from a light source through a sample of the water held in a receptacle, the sample being between the spaced apart opposing windows, said light source emitting light at a specific wavelength, wherein the specific wavelength of the light source corresponds to the specific halogen whose concentration is being monitored, said optical absorption analyzer comprising a processing unit configured for:
      i. deriving the concentration of the specific halogen at least in part by processing results of the measurements of transmission of ultraviolet light from a light source through the sample of water; and
      ii. releasing a signal conveying the derived concentration of the specific halogen.

2. A device as defined in claim 1, wherein the spaced apart opposing windows are made of at least one of quartz, optical glass, cellulose diacetate, polyethylene, acrylic and polyester.

3. A device as defined in claim 1, wherein the measurements of transmission of ultraviolet light include a first measurement of transmission of ultraviolet light and a second measurement of transmission of ultraviolet light, and wherein the optical absorption analyzer further comprises:
   i. the light source for emitting ultraviolet light at the specific wavelength;
   ii. a first detector for making the first measurement of transmission of ultraviolet light from said light source through the sample of water;
   iii. a second detector for making the second measurement of transmission of ultraviolet light, wherein the second measurement is taken prior to the ultraviolet light travelling through the sample of water.

4. A device as defined in claim 3, wherein said light source is a first light source and wherein said specific wavelength is a first specific wavelength, said optical absorption analyzer further comprising a second light source for emitting light at a second specific wavelength different from the first specific wavelength, wherein:
   a. the first detector is used for making a first measurement of transmission of light from the second light source through the sample of water;
   b. the second detector is used for making a second measurement of transmission of light from said second light source, wherein the second measurement is taken prior to the light from said second light source travelling through the sample of water;
   c. the processing unit is configured to derive the concentration of the specific halogen by processing at least:
      i. results of the first and the second measurements of transmission of light from said second light source; and
      ii. the results of the first and the second measurements of transmission of light from said first light source.

5. A device as defined in claim 4, wherein said optical absorption analyzer further comprises a beam splitter module for directing:
   i. a first part of ultraviolet light generated by said first light source toward the first detector through the sample of water;
   ii. a second part of ultraviolet light generated by said first light source toward the second detector;
   iii. a first part of light generated by said second light source toward the first detector through the sample of water; and iv. a second part of light generated by said second light source toward the second detector.

6. A device as defined in claim 4, wherein said second specific wavelength at which said second light source emits light is between about 450 nm and 1100 nm.

7. A device as defined in claim 6, wherein said second specific wavelength at which said second light source emits light is between about 475 nm and 550 nm.

8. A device as defined in claim 4, wherein the first light source and the second light source are modulated light sources.

9. A device as defined in claim 4, wherein the first light source and the second light source are configured to emit light according to sinusoidal light patterns.

10. A device as defined in claim 9, wherein the first light source is modulated at a first frequency and the second light source is modulated at a second frequency, wherein the first frequency is different from the second frequency and wherein said processing unit is configured for deriving the concentration of the specific halogen at least in part based on a frequency distribution associated with:
   a. the results of the first and the second measurements of the transmission of light from said first light source; and
   b. the results of the first and the second measurements of the transmission of light from said second light source.

11. A device as defined in claim 10, wherein the first frequency of the first light source is between 420 and 580 Hz.

12. A device as defined in claim 11, wherein the second frequency of the second light source is between 540 and 600 Hz.

13. A device as defined in claim 3, wherein said optical absorption analyzer further comprises:
   i. a beam splitter module for directing:
   ii. a first part of ultraviolet light generated by said light source toward the first detector through the sample of water; and
   iii. a second part of ultraviolet light generated by said light source toward the second detector.

14. A device as defined in claim 1, wherein said optical absorption analyzer further comprises a temperature sensor for generating a signal conveying water temperature information for the sample of water, said processing unit being configured for deriving the concentration of the specific halogen at least in part by processing the results of the measurements of transmission of ultraviolet light and of the water temperature information.

15. A device as defined in claim 1, wherein the specific halogen whose concentration is being monitored is selected from the group consisting of chlorine and bromine.

16. A device as defined in claim 15, wherein the specific halogen whose concentration is being monitored is bromine.

17. A device as defined in claim 16, wherein the specific wavelength at which said light source emits light is between about 280 nm and 380 nm.

18. A device as defined in claim 17, wherein the specific wavelength at which said light source emits light is between about 300 nm and 360 nm.

19. A device as defined in claim 18, wherein the specific wavelength at which said light source emits light is about 310 nm.

20. A device as defined in claim 1, wherein said upper portion includes a display screen in electronic communication with the processing unit of said optical absorption analyzer for displaying information derived from the derived concentration of the specific halogen.

21. A device as defined in claim 1, further comprising an antenna for transmitting the signal conveying the derived concentration of the specific halogen to a remote device, said remote device including a display for conveying the derived concentration of the specific halogen.

22. A device as defined in claim 21, wherein said remote device is a smart phone.

23. A device as defined in claim 1, wherein said device is configured to transmit the signal conveying the derived concentration of the specific halogen to a processing module external to the device over a wireless link, said processing module external to the device being configured for using the derived concentration of the specific halogen to control generation of the specific halogen to detect at least one of an excess and an insufficiency of the specific halogen in the water.

24. A device as defined in claim 23, wherein said processing module external to the device being configured for controlling generation of the specific halogen by controlling operation of an electrolytic cell.

\* \* \* \* \*